United States Patent
Friedli et al.

(10) Patent No.: US 10,166,333 B2
(45) Date of Patent: Jan. 1, 2019

(54) METHOD FOR GENERATING A MONITORING SIGNAL USING A SUPERVISING ENTITY OR SAFETY MODULE

(71) Applicant: Roche Diabetes Care, Inc., Indianapolis, IN (US)

(72) Inventors: Kurt Friedli, Mannheim (DE); Carsten Mueglitz, Schoenau (DE); Ralf Schmitz, Weinheim (DE); Kai-Oliver Schwenker, HaBloch (DE); Thomas Eissenloeffel, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 15/508,302

(22) PCT Filed: Sep. 11, 2015

(86) PCT No.: PCT/EP2015/070847
§ 371 (c)(1),
(2) Date: Mar. 2, 2017

(87) PCT Pub. No.: WO2016/041863
PCT Pub. Date: Mar. 24, 2016

(65) Prior Publication Data
US 2017/0290980 A1    Oct. 12, 2017

(30) Foreign Application Priority Data
Sep. 15, 2014    (EP) .................................... 14184795

(51) Int. Cl.
*A61M 5/172*      (2006.01)
*G16H 40/40*      (2018.01)
(Continued)

(52) U.S. Cl.
CPC ........... *A61M 5/1723* (2013.01); *A61B 5/747* (2013.01); *G06F 19/00* (2013.01);
(Continued)

(58) Field of Classification Search
CPC .......... A61B 2560/0223; A61B 5/0031; A61B 5/1411; A61B 5/14503; A61B 5/1451;
(Continued)

(56) References Cited

U.S. PATENT DOCUMENTS

2008/0300919 A1    12/2008 Charlton et al.
2009/0076358 A1    3/2009 Reggiardo et al.
(Continued)

OTHER PUBLICATIONS

International Patent Application PCT/EP2015/070847 International Preliminary Report on Patentability and Written Opinion dated Mar. 30, 2017. 8 pages.

*Primary Examiner* — Manuel A Mendez
(74) *Attorney, Agent, or Firm* — Woodard, Emhardt, Moriarty, McNett & Henry, LLP

(57) ABSTRACT

The present invention relates to method for generating a monitoring signal by monitoring laboratory values of a patient using a medical app (122). The medical app (122) is executed on a mobile device (102) of the patient, wherein the execution of the medical app (122) on the mobile device (102) of the patient is supervised by a supervising entity or safety module (106, 128), the supervising entity or safety module (106, 128) comprising at least executable program instructions (130). The medical app (122) comprises executable instructions for executing at least one sequence of processes for generating the monitoring signal. The processes comprise safety critical processes. The sequence of processes is triggered by the measurement of the blood glucose level of the patient. The method comprises executing a first process of the sequence of processes, wherein the execution results in the generation of an information, for- (Continued)

warding the information of the executed process to the supervising entity or safety module (106, 128), evaluating the received information by the supervising entity or safety module (106, 128) and executing a second process of the sequence of processes depending on the result of the evaluation.

18 Claims, 14 Drawing Sheets

(51) Int. Cl.
    *G06F 19/00*     (2018.01)
    *A61B 5/00*     (2006.01)
    *G16H 50/20*     (2018.01)

(52) U.S. Cl.
    CPC ......... *G06F 19/3468* (2013.01); *G16H 40/40* (2018.01); *A61M 2205/18* (2013.01); *A61M 2205/3368* (2013.01); *A61M 2205/3553* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/587* (2013.01); *A61M 2230/201* (2013.01); *G16H 50/20* (2018.01)

(58) Field of Classification Search
    CPC .............. A61B 5/14532; A61B 5/1468; A61B 5/14865; A61B 5/1495; A61B 5/4839; A61B 5/7221; A61B 5/747; A61M 2230/201; A61M 5/1723; C12Q 1/006; C12Q 1/54; G06F 19/34; G06F 19/3412; G06F 19/3468; Y10S 435/817
    USPC ..................... 600/365; 604/65–67, 131, 151; 128/DIG. 1, 12, 13
    See application file for complete search history.

(56) References Cited

U.S. PATENT DOCUMENTS

2012/0116196 A1\* 5/2012 Tubb .................. A61B 5/14532
    600/365
2014/0163919 A1     6/2014 Manigel et al.

\* cited by examiner

METHOD FOR GENERATING A MONITORING SIGNAL USING A SUPERVISING ENTITY OR SAFETY MODULE

FIELD OF THE INVENTION

The present invention relates to the generating of a monitoring signal by monitoring laboratory values of a patient using a medical app, wherein the execution of the medical app is supervised by a supervising entity or safety module and a medical system, such as an infusion pump system, in particular an insulin pump system.

BACKGROUND AND RELATED ART

Nowadays medical devices like for example insulin pumps get smaller and smaller. As a result the controls of such a small medical device may get too small to be used manually by a patient. Therefore in some cases it is useful to control these medical devices using a separate device like for example a mobile device, which is connected to the medical device. For example medical devices can nowadays be controlled using a smartphone. However, as medical devices may perform life critical actions like applying a medication to a patient, it may be necessary to supervise the execution of the medical app running on a smartphone as smartphones in general are not developed in accordance with medical safety guidelines like IEC 62304.

An infusion pump is a medical device that delivers fluids, such as nutrients and medications, into a patient's body in controlled amounts. Infusion pumps are in widespread use in clinical settings such as hospitals, nursing homes, and in the home.

In general, an infusion pump is operated by a trained user, who programs the rate and duration of fluid delivery through a built-in software interface. Infusion pumps offer significant advantages over manual administration of fluids, including the ability to deliver fluids in very small volumes, and the ability to deliver fluids at precisely programmed rates or automated intervals. They can deliver nutrients or medications, such as insulin or other hormones, antibiotics, chemotherapy drugs, and pain relievers.

There are many types of infusion pumps, including large volume, patient-controlled analgesia (PCA), elastomeric, syringe, enteral, and insulin pumps. Some are designed mainly for stationary use at a patient's bedside. Others, called ambulatory infusion pumps, are designed to be portable or wearable.

Because infusion pumps are frequently used to administer critical fluids, including high-risk medications, pump failures can have significant implications for patient safety. Many infusion pumps are equipped with safety features, such as alarms or other operator alerts that are intended to activate in the event of a problem. For example, some pumps are designed to alert users when air or another blockage is detected in the tubing that delivers fluid to the patient. Some newer infusion pumps, often called smart pumps, are designed to alert the user when there is a risk of an adverse drug interaction, or when the user sets the pump's parameters outside of specified safety limits.

Insulin pump therapy is often referred to as "Continuous Subcutaneous Insulin Infusion" (CSII) and closely imitates the natural action of the pancreas, providing a constant supply of insulin to the body and extra doses as needed.

When using a portable insulin pump, there is no longer any need for injections. Instead the pump is controlled to continuously supply a patient's body with the insulin it requires by way of a subcutaneous cannula (under the skin).

One approach for controlling the program flow of a computer program is known as "COMEFROM" programming. In this case the individual sub-processes of a computer program hand over intermediate results of the execution of the sub-process to a subsequent process wherein the addressed process may then verify whether the process calling is actually allowed to call the subsequent process. As a result the whole execution of a computer program is controlled by the individual modules of the computer program verifying if they are activated in the correct order. As soon as there is not only one sequence of processes involved but more than one, wherein the individual processes of both sequences affect each other, the COMEFROM from approach will not work anymore as there is usually no communication between the modules of the individual sequences. As it may further be possible that some processes of a first sequence of processes may only be executed if a series of individual process of another sequence of processes have already been executed, the COMEFROM approach is not sufficient anymore.

SUMMARY

The invention provides for a method for generating a monitoring signal by monitoring laboratory values of a patient using a mobile device and a supervising entity or safety module as well as a corresponding system comprising a mobile device and a supervising entity or safety module. Embodiments of the invention are given in the dependent claims.

The present patent application claims the priority of EP14184795 the entirety of which being herein incorporated by reference.

In accordance with embodiments of the invention a monitoring signal is generated by monitoring laboratory values of a patient using a medical app. The medical app is executed on a mobile device of a patient, wherein the execution of the medical app on the mobile device of the patient is supervised by a supervising entity. The supervising entity comprises at least executable program instructions and the medical app comprises executable instructions for executing at least one sequence of processes, wherein the processes comprise processes for measuring at least one laboratory value of a patient, comparing the measured values to predefined ranges of permitted values and in response to determining that at least one of the measured values is beyond the predefined range generating the monitoring signal. The method for generating the monitoring signal further comprises the steps of executing a first process of the sequence of processes wherein the execution results in the generation of an information. The information of the executed process is then forwarded to the supervising entity and evaluated by the supervising entity. Depending on the result of the evaluation a second process of the sequence of processes may then be executed.

In accordance with embodiments of the invention a monitoring signal is generated by monitoring laboratory values of a patient using a medical app. The medical app is executed on a mobile device of a patient, wherein the execution of the medical app on the mobile device of the patient is supervised by a supervising entity or safety module. The supervising entity or safety module comprises at least executable program instructions and the medical app comprises executable instructions for executing at least one sequence of processes for generating the monitoring signal, wherein the processes comprise safety critical processes. The sequence of processes is triggered by the measurement of the blood glucose level of the patient. In some embodiments the sequence of processes comprises processes for measuring or determining at least one laboratory value of a patient, comparing the measured or determined value to predefined ranges of permitted values and in response to determining that at least one of the measured or determined values is beyond the predefined range generating the monitoring signal. The method for generating the monitoring signal further comprises the steps of executing a first process of the sequence of processes wherein the execution results in the generation of an information. The information of the executed process is then forwarded to the supervising entity or safety module and evaluated by the supervising entity or safety module. Depending on the result of the evaluation a second process of the sequence of processes may then be executed.

Embodiments of the invention may have the advantage that a central supervising entity or safety module is introduced wherein each executed process provides an information to the supervising entity or safety module. Depending on this information the supervising entity or safety module may then determine whether a next process of the sequence of processes may be executed. It has to be noted that this also works for more than one sequence of processes being executed in parallel. For example if there are two sequences the supervising entity or safety module receives information from processes of both sequences and may then decide based on both these information whether subsequent processes may be executed. As a result it may for example be possible that a process in the first sequence of processes is only executed if a number of processes in the second sequence have already been executed as indicated by the information provided to the supervising entity or safety module. Thus, especially safety critical processes are only executed if all requirements for their execution are fulfilled like for example the prior execution of other processes.

In this context a safety critical process can be understood as a process which may harm a patient in case the process is not executed correctly. Assume for example that the mobile device is the smart phone of a patient, the patient suffering from diabetes. The medical application which is running on the smartphone may for example be adapted to receive measurement data from a continuous glucose measurement entity which is implanted into the tissue of the patient. Using this measurement data the medical application may for example determine the current blood glucose value and display corresponding information to the patient. Using this blood glucose value the medical app may indicate the necessity of injecting insulin into the patient's tissue.

In case the medical app is not working as expected it may occur, that faulty blood glucose values are displayed to the patient causing the patient to inject insulin. As this may cause serious harm to the patient the process for determination of the blood glucose value of the patient as well as the process for emitting warnings has to be supervised. Thus the determination of a blood glucose value as well as the monitoring of warning limits can be understood as safety critical processes. Further safety critical processes may for example be the calibration of the blood glucose measurement, the pairing of the smart phone with a module like the safety module or the initialization of the continuous blood glucose measurement sensor. Further the smart phone or the medical may comprise self-test sequences like run-time tests and power-on self-tests which also have to be supervised.

The monitoring signal generated during execution of the method may have a number of effects. In some embodiments the monitoring signal is adapted to trigger the mobile device to make an emergency call. This may for example by advantageous if the medical app monitors laboratory values like a pulse of the patient or oxygen saturation of the blood or blood glucose levels or any other vital signs wherein the determining that the measured or determined values are beyond a predefined range may indicate a life endangering state of the patient. By using an automated emergency call as soon as a measured or determined value drops out of a predefined range may then reduce the response time of for example a rescue service.

In some embodiments the mobile device is connected to a medical device of the patient wherein the monitoring signal is adapted to trigger the medical device to apply a medication or stop applying medication to the patient such that the laboratory values of the patient are moved into the perimeters of the predefined range. For example the medical device may be an insulin pump wherein the monitoring is directed towards the blood glucose level of the patient. As soon as the medical app detects that the glucose level of the blood of the patient is too high or too low the medical app may then activate, deactivate, speed up or slow down the medical device which in this case may be the insulin pump such that the patient is provided with a sufficient amount of insulin. This general approach may be advantageous if the laboratory value which is being monitored represents a vital function which may be recovered by applying medication.

In the example of an insulin pump a safety critical process may for example be the setting of a basal rate or temporal basal rate for injecting insulin, the measuring of the blood glucose level by the medical device itself, the setting of an insulin bolus, starting/stopping the application of insulin and the initializing process for example after the infusion unit has been changed.

In yet another embodiment the monitoring signal is adapted to trigger the mobile device to emit a perceivable alarm signal. If the medical app for example monitors a laboratory value which is not directly life critical, like for example the temperature of the patient, it may be sufficient to just give off an alarm if the temperature of the patient is too high or too low as usually it is not necessary to directly counteract the too high or too low body temperature of the patient.

In some embodiments the execution of the first process results in the generation of an intermediate result wherein the intermediate result is passed on to the second process of the sequence of processes for further processing. The information then comprises the intermediate result wherein the supervising entity or safety module verifies whether the intermediate result received with the information is within a defined range of results. Further, the second process of the sequence of processes is only executed if the result has been determined to be within the defined range of results.

For example a sequence of processes which shall ultimately lead to the generation of the monitoring signal may start with the first process which is meant to receive measurement data from a medical device and convert the received data into a format readable by the subsequent processes. Once this first process has finished the process forwards the result that is the converted data received from the medical device to the supervising entity or safety module. The supervising entity or safety module may then comprise a table, wherein the table comprises information on the format the result of the first process should be in or the table may further comprise information on a range of results which is to be expected when executing the first process.

The supervising entity or safety module may then verify whether the format of the received result as well as the value of the received result is within the allowed boundaries and if so may allow the second process to be executed. Further, the supervising entity or safety module may be adapted to forward the result of the first process to the second process such that it is not possible to execute the second process without involving the supervising entity or safety module. However the processes may also hand over intermediate results directly to the subsequent process.

In some embodiments the supervising entity or safety module generates a trigger signal in response to determining that the result is within the predefined range and transmits the trigger signal to the mobile device. The trigger signal when received by the mobile device then triggers the mobile device to execute the second process. This may have the advantage that the second process can only be executed if the supervising entity or safety module already has received the intermediate result from the first process and verified that the received intermediate result is within the predefined range thereby verifying that the execution of the sequence of processes is not flawed.

In some embodiments the supervising entity or safety module brings the mobile device into a failsafe state, i.e. into a safe state or into a safe operational mode with reduced functionality, eliminating the faulty functionality from the overall system function in response to determining that the intermediate result is not within the defined range of results. This may have the advantage that a faulty execution of the sequence of processes will not affect the patient in a hazardous or life critical way as soon as the supervising entity or safety module detects that one of the processes of the sequence of processes does not work as expected it brings the mobile device into a safe state or safe operational mode with reduced functionality, thereby avoiding any further actions which may harm the patient.

In some embodiments identifiers are assigned to the processes of the sequence wherein the supervising entity or safety module is operable to access a sequence table. The sequence table comprises entries specifying allowed sequences of processes or forbidden sequences, wherein the information the supervising entity or safety module receives from the executed processes comprises the identifier of the second process, which shall be executed subsequent to the first process. The supervising entity or safety module then verifies whether the second process may be executed subsequent to the first process by looking up the sequence table. In response to determining that the second process is not allowed to be executed subsequent to the first process, the supervising entity or safety module then interrupts the execution of the sequence.

It may further be possible that the processes in response to being executed forward their identifier to the supervising entity or safety module, such that the supervising entity or safety module may verify whether the process which has just been started is actually allowed to be executed. In this case it may be necessary that the reaction time of the supervising entity or safety module is lower than the execution time of the process, as in the opposite case, the supervising entity or safety module will not be able to interrupt the execution of the process before the process comes to an end.

Embodiments may have the advantage that by verifying the identifiers of the processes and checking whether the processes are executed in the correct order, no processes will be executed too early, for example prior to the execution of another process, which is necessary for the execution of the second process. As a result a skipping of a critical process can be avoided. In this case, it is also possible that the sequence table comprises entries specifying processes of another sequence which have to be executed prior to the execution of a process of a first sequence. Thus the supervising entity or safety module is also operable to verify the correct order of execution of processes of a plurality of sequences.

In some embodiments the supervising entity or safety module is adapted to create a log file during execution of a sequence of processes. The log file comprises the identifiers of processes which have already been executed in course of the execution of the sequence or sequences of processes.

Embodiments may have the advantage that if the sequence of processes has to be interrupted due to an incorrect execution of processes, it is possible to recreate the situation which led to the failure of the medical app. To this end it is only necessary to check which processes have successfully been executed and at which process the execution came to an end.

In some embodiments the sequence table further comprises information specifying a set of processes which have to be executed prior to the execution of the second process, wherein the supervising entity or safety module further verifies whether the set of processes has already been executed by looking up the sequence table and comparing the identifiers of the set of processes with the identifiers comprised in the log file. Embodiments may facilitate verification whether all relevant process steps have already been executed prior to the starting of the execution of the second process.

In some embodiments the supervising entity or safety module deletes the log file if the sequence of processes, which has to be executed during execution of the medical app, has been completed successfully. This may have the advantage that no disk space of the mobile device is wasted by storing log files which are not needed anymore.

In some embodiments the supervising entity or safety module brings the mobile device into a failsafe state, i.e. into a safe state in response to determining that the second process is not allowed to be executed subsequent to the first process. In accordance with some embodiments the safe state is characterized in that in the safe state the functionality of the mobile device is reversibly reduced such that the mobile device is no longer operable to make an emergency call and/or trigger a medication device to apply or stop or change medication and/or emit a perceivable alarm signal while in the safe state. Further it is possible that the safe state is maintained for a predefined period of time or is maintained until a system administrator examined why the execution of the medical app had to be aborted due to a failure in execution. It is also possible that when bringing the mobile device into the safe state the mobile device or the supervising entity or safety module automatically transmits a notifying message to an administrator of the medical device or the mobile device indicating that the execution of the medical app had to be stopped due to an error during execution and providing further details of the situation in which the execution had to be aborted. For example the notification may comprise the IDs of the processes which have already been executed or may comprise the process which has produced a result that is not within the predefined ranges of acceptable results.

In some embodiments the supervising entity or safety module is operable to address the mobile device to conduct a data processing algorithm. The supervising entity or safety module further provides the mobile device with data for processing using the data processing algorithm, wherein the mobile device in response to be addressed by the supervising entity or safety module conducts the data processing algorithm thereby generating a result. The supervising entity or safety module in response to the mobile device generating the result verifies the result and in response to successfully verifying the result triggers the mobile device to execute the second process. For example, the supervising entity or safety module may ask the mobile device to conduct a simple mathematical operation with given starting values, wherein the supervising entity or safety module may for example have the result of the mathematical equation for the given values already in store. By comparing the result of the execution by the mobile device with the result, which is stored in the supervising entity or safety module, the supervising entity or safety module may check whether the mobile device operates as expected. If for example the processing unit of the mobile device does not operate as expected, the result of the demanded data processing algorithm with the given data will differ from the result which is stored in the supervising entity or safety module. Thus by asking the mobile device to conduct data processing, wherein the result is already known by the supervising entity or safety module, it is possible to verify whether the processing entity of the mobile device is still working correctly.

In some embodiments the supervising entity or safety module addresses the mobile device to conduct the data processing algorithm as described above, if no allowed range for the intermediate result of the execution of a process of the sequence of processes received with the information is defined. This may have the advantage that even if it is not possible to verify the result as such, it is possible to verify the correct functionality of the processing entity of the mobile device. Therefore a faulty execution of the sequence of processes can be detected without verifying the correct sequence of processes or verifying the correct range of results.

In some embodiments the mobile device is connected to a measurement entity, wherein the mobile device, when executing the process of measuring at least one laboratory value of the patient, addresses the measurement entity to conduct the corresponding measurement and return corresponding measurement values. For example, the mobile device may be connected to the measurement entity using a wireless data communication method, which may increase the usability of a system of a mobile device and a measurement entity as no cable connection is necessary.

In another aspect the invention provides a system comprising a mobile device being connected to a supervising entity, wherein the mobile device is operable to execute at least one medical app, wherein the execution of the medical app on the mobile device is supervised by the supervising entity, the supervising entity comprising at least executable program instructions, the medical app comprising executable instructions for executing at least one sequence of processes, the processes comprising processes for:
  measuring at least one laboratory value of the patient
  comparing the measured values to predefined ranges of permitted values and
  in response to determining that at least one of the measured values is beyond the predefined range generating the monitoring signal.

Further, the mobile device is operable to execute a first process of the sequence of processes, wherein the execution results in the generation of an information and to forward the information to the supervising entity, wherein the supervising entity is adapted to evaluate the information, wherein the mobile device is further adapted to execute the second process of the sequence of processes depending on the result of the evaluation.

In another aspect the invention provides a system comprising a mobile device being connected to a supervising entity or safety module, wherein the mobile device is operable to execute at least one medical app, wherein the execution of the medical app on the mobile device is supervised by the supervising entity or safety module, the supervising entity or safety module comprising at least executable program instructions, the medical app comprising executable instructions for executing at least one sequence of processes for generating the monitoring signal, the processes comprising safety critical processes, the sequence of processes being triggered by the measurement of the blood glucose level of the, the mobile device being operable to execute a first process of the sequence of processes, wherein the execution results in the generation of an information and to forward the information to the supervising entity or safety module, wherein the supervising entity or safety module is adapted to evaluate the information, wherein the mobile device is further adapted to execute the second process of the sequence of processes depending on the result of the evaluation.

In some embodiments the supervising entity or safety module comprises at least one processor, a telecommunication interface and a memory wherein the memory comprises at least executable instructions for evaluating the information. The processor of the supervising entity or safety module is further adapted to execute the executable instructions comprised in the memory and the supervising entity or safety module is adapted to communicate with the mobile device using the communication interface. For example the supervising entity or safety module may be embodied in a smart card, a secure element, a hardware security module or a plug-in module which can be attached to the mobile device.

The telecommunication interface may for example be adapted to communicate with the mobile device via Bluetooth™ Low Energy (BLE). Using BLE for the communication between the supervising entity or safety module and the mobile device may have the advantage that the supervising entity or safety module can be powered with for example a single button cell as the communication using BLE consumes only little amounts of battery power. Thus the supervising entity or safety module could be used over large periods of time without having to change or reload the battery. As the data traffic between the supervising entity or safety module and the mobile device can be kept at a very low level, the reduced bandwidth of BLE is no limiting factor for its application according to the invention.

Possible further feature combinations of embodiments of the invention may be the following:
  1. A method for supervising the execution of a sequence of processes by a supervising entity or safety module, the supervising entity or safety module being operatively coupled to a medical device, the method comprising:
      receiving a first information generated in course of the execution of a first process of the sequence of processes from the medical device,
      evaluating the received first information, and
      transmitting a second information indicative of an authorization or denial to execute of a second process of the sequence of processes to the medical device, the second process succeeding the first process in the sequence of processes.

2. The method of feature combination 1, the first information being indicative of an intermediate result determined in course of execution of the first process, the intermediate result being used when executing the second process, the evaluating the received first information comprising verifying whether the intermediate result is within a predefined range of results, wherein the second information is indicative of an authorization for execution of the second process in case the result has been determined to be within the defined range of results.

3. The method of feature combination 2, wherein in response to determining that the intermediate result is within the predefined range the second information is operable to trigger the medical device to execute the second process and wherein in response to determining that the intermediate result is not within the defined range of results, second information is operable to trigger the medical device to put itself into a safe state.

4. The method of any of the preceding feature combinations, wherein identifiers are assigned to the processes of the sequence, wherein the supervising entity or safety module is adapted to access a sequence table comprised in the supervising entity or safety module, the sequence table comprising entries specifying allowed sequences of processes, wherein the first information comprises the identifier of the second process, wherein the supervising entity or safety module verifies whether the second process may be executed subsequent to the first process by looking up the sequence table, and wherein only in response to determining that the second process is allowed to be executed subsequent to the first process the second information comprises an authorization.

5. The method of feature combination 4, the supervising entity or safety module being adapted to create a log file during execution of the sequence of processes, the log file comprising the identifiers of processes which have already been executed in course of the execution of the sequence of processes.

6. The method of feature combination 5, the sequence table further comprising information specifying a set of processes which have to be executed prior to the execution of the second process, wherein the method further comprises verifying whether the set of processes has been executed by looking up the sequence table and comparing the identifiers of the set of processes with the identifiers comprised in the log file, wherein the second information is only indicative of an authorization in case it is determined that the set of processes has been executed.

7. The method of any of the preceding feature combinations, the evaluating the first information comprising:
transmitting a third information indicative of data processing algorithm and corresponding data for processing to the medical device for execution,
receiving the result from the execution of the data processing algorithm from the medical device, and verifying the received result,
wherein the second information is only indicative of an authorization in case the received result is determined to be correct.

8. A supervising entity or safety module being adapted to execute the method in accordance with any of the preceding feature combinations.

9. A computer program product comprising machine executable instructions for performing the method of any of the preceding feature combinations 1-7.

In still another aspect the present invention relates to a medical system comprising an infusion pump for the delivery of a fluid, such as a nutrient and/or medication, such as insulin, into a patient's body. The infusion pump has a communication interface for receiving a control parameter for controlling the rate of delivery of the fluid. The infusion pump is configured for coupling with a mobile device that has a respective communication interface for communicating with the infusion pump. The mobile device may be implemented as a mobile battery-powered handheld electronic appliance, such as a mobile telecommunication device, in particular a mobile battery powered handheld telecommunication device, such as a smartphone. In particular, the mobile device may be configured for coupling to a digital wireless cellular telecommunication network and/or a wireless local area network.

The communication interface of the mobile device for communicating with the infusion pump may be configured for establishing a direct communication link with the infusion pump without the intermediary of a network. For example the mobile device's communication interface with the infusion pump may be configured for establishing a wired or wireless connection, such as in accordance with an RFID, NFC or Bluetooth standard, in particular in accordance with VLE.

The mobile device is configured for executing of an application program that is installed on the mobile device. The application program may be implemented as a so called 'app' that can be downloaded from an app store onto the mobile device, especially if the mobile device runs an Android or Apple iOS operating system. The application program that is installed on the mobile device serves for controlling the infusion pump and is thus referred to as 'medical app' in the following.

The mobile device is also coupled to a sensor that is configured for sensing at least one physiological parameter of the patient. The sensor and/or the infusion pump may be implantable into the patient's body and may be formed as a single integrated implant or separate implants, such as for subcutaneous implantation.

The sensor may have a separate communication interface for communicating with the respective communication interface of the mobile device or it may form an integral part of the infusion pump such that the communication of the sensed physiological parameter from the sensor to the mobile device is performed by means of the communication interface of the infusion pump.

Further, the medical system comprises a testing module for testing the mobile device. Such a testing module may be implemented as a supervising entity or safety module as explained above.

In particular, the testing module may be implemented as a hardware module that is separate from the mobile device. The hardware module may be battery-powered and may have a communication interface for communicating with the respective communication interface of the mobile device such as in accordance with a Bluetooth standard, in particular a BLE.

The hardware module comprises a microprocessor for executing a program that implements a testing routine for testing whether the mobile device is in a functional state. The mobile device may leave its normal functional state for example due to an error of the mobile device's operating system, in particular an error that has been introduced by updating the operating system, by the installation of an additional app that causes malfunctioning of the mobile device and/or that contains malicious software, such as a virus, by receipt of a message, such as an email or SMS, by a mobile device that contains malicious software or data, such as a virus, or due to another software and/or hardware failure of the mobile device. For example, the testing routine may comprise a validation activity where the correct solution of a validation problem solved by the mobile device is checked by the hardware module.

In operation, the mobile device receives the value of the physiological parameter that has been sensed by the sensor. This value of the physiological parameter received by the mobile device from the sensor is entered into the medical app by the mobile device. In response to receipt of the value of the physiological parameter by the mobile device and its entry into the medical app, the medical app is executed for determining a value of the control parameter for controlling the infusion pump whereby the medical app implements a control algorithm that uses the physiological parameter as an input value. Next, the value of the control parameter which has thus been determined is sent from the medical app via the communication interface of the mobile device to the infusion pump for adjusting the rate of fluid delivery of the infusion pump in accordance with the determined control parameter value.

In order to protect the patient against a malfunctioning mobile device, the medical app is configured to transmit a testing request to the testing module before sending the control parameter to the infusion pump. The testing request invokes execution of the testing routine by the testing module which returns a positive testing result if the mobile device is in a functional state. This protects the patient against a malfunctioning mobile device that could determine an incorrect value of the control parameter which in turn could have serious consequences for the patient's health.

Embodiments of the present invention are particularly advantageous as the invention enables to utilize a mobile device that may be a consumer device not developed in accordance with medical safety guidelines, such as a smartphone, for controlling an infusion pump in a safe manner. This is accomplished by checking the state of the mobile device by a testing module that may be implemented as a separate hardware entity which is designed in accordance with medical safety guidelines.

The testing module may be invoked for performing testing of the mobile device multiple times before the value of the control parameter is send to the infusion pump, such as in response to receipt of the value of the sensed physiological parameter, before the value of the sensed physiological parameter is displayed on a screen of the mobile device and/or before the control algorithm that uses the physiological parameter as an input value is executed by execution of the medical app.

In accordance with embodiments of the invention the medical system is an insulin pump system, wherein the infusion pump is an insulin infusion pump for delivery of insulin into the patient's body and the sensor is a subcutaneous sensor for sensing the blood glucose level of the patient.

It is understood that one or more of the aforementioned embodiments of the invention may be combined as long as the combined embodiments are not mutually exclusive.

BRIEF DESCRIPTION OF THE DRAWINGS

In the following, embodiments of the invention are explained in greater detail by way of example only, making reference to the drawings in which.

Like numbered elements in these Figs. are either equivalent elements or perform the same function. Elements which have been discussed previously will not necessarily be discussed in later Figs. if the function is equivalent.

DETAILED DESCRIPTION

Figure 1:
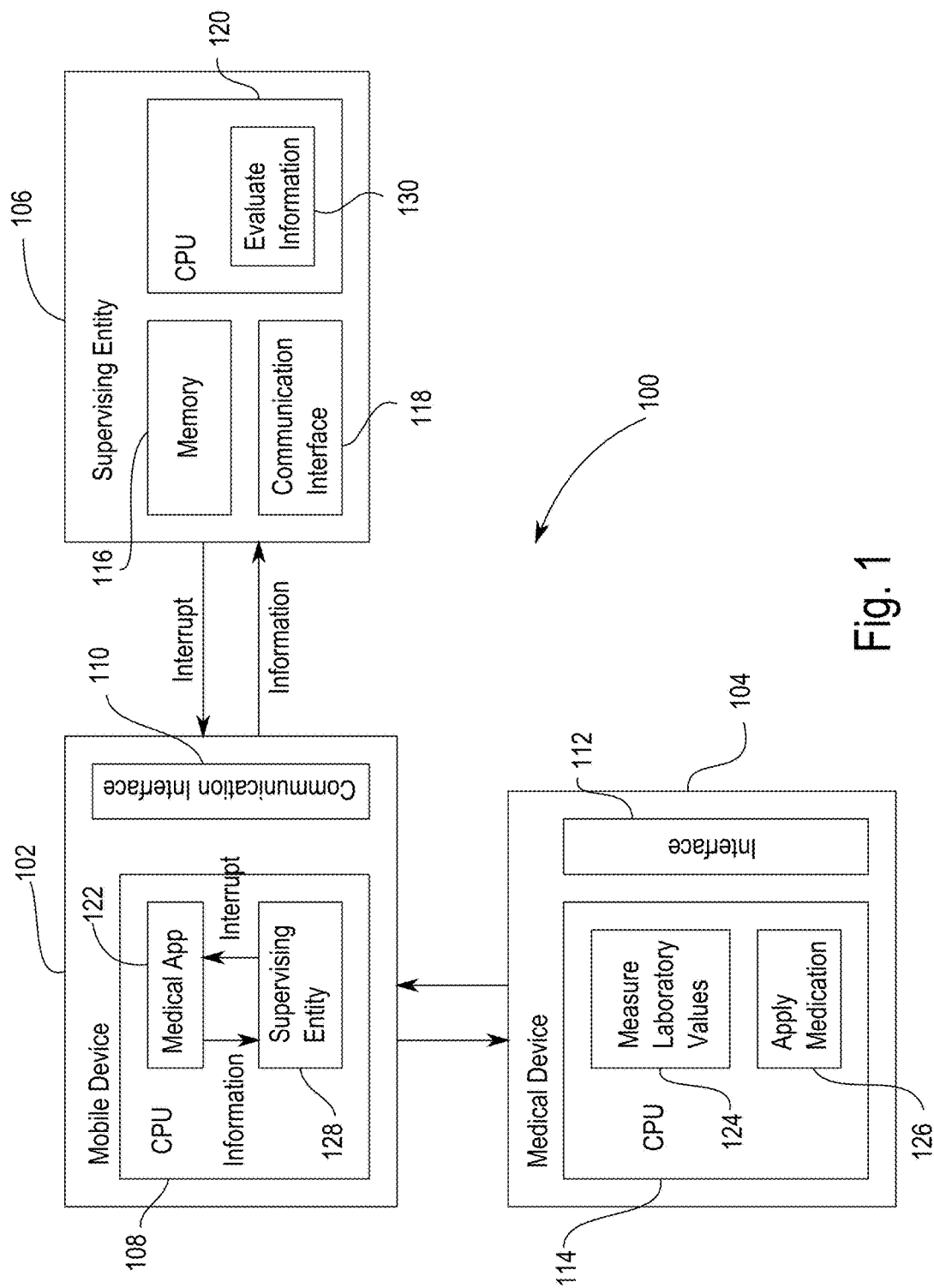
FIG. 1 is a block diagram of a system comprising a mobile device, a supervising entity or safety module and a medical device.

FIG. 1 illustrates an example of a system 100 comprising a mobile device 102, a medical device 104 and a supervising entity or safety module 106. The mobile device 102 comprises a central processing unit 108 and a communication interface 110. Via the communication interface 110 the mobile device 102 can be connected to the medical device 104. The medical device 104 comprises an interface 112 for communicating with the mobile device 102 and further comprises a central processing unit 114. The mobile device 102 is further connected via the communication interface 110 to the supervising entity or safety module 106.

The supervising entity or safety module 106 comprises a memory 116 as well as a communication interface 118 and a central processing unit 120.

For monitoring the laboratory values of a patient the central processing unit 108 of the mobile device 102 comprises a program module further referred to as medical app 122. The medical app 122 is operable to demand laboratory values of a patient using the communication interface 110 from a medical device 104. The medical device 104 when being addressed by the medical app 122 of the mobile device 102 may then execute a program module 124 for measuring laboratory values of the patient. The execution of the program module 124 by the central processing unit 114 of the medical device 104 may then result in the collection of data representative of for example blood values of the patient like the blood glucose level or the oxygen saturation or other data specifying the current condition of the patient. Once this data has been collected by medical device 104 the medical device 104 forwards the collected data to the mobile device 102 using the interfaces 112 and 110. The medical app 122 may then process the received data in order to verify whether the laboratory value calculated from the received data is within a predefined range. For example the medical app 122 may verify whether the blood glucose level of the patient is too high or too low.

If the medical application 122 determines that the blood glucose level is outside the predefined ranges, the medical app 122 may then address the medical device 104 to initiate counter measures by generating a corresponding monitoring signal and forwarding the signal to the medical device 104. Upon receiving the monitoring signal the medical device 104 may then execute a further program module 126 using the central processing unit 114. The execution of the program module 126 may then cause the medical device 104 to apply a medication to the patient in order to affect the patient such that the laboratory value shifts into the predefined range. For example if the medical app 122 determined that the blood glucose level of the patient is too high the execution of the program module 126 may cause the medical device 104 to inject insulin into the patient's tissue.

It is also possible that the medical app 122 upon determining that a laboratory value of the patient is outside the predefined range triggers the mobile device 102 to make an emergency call. To this end the mobile device 102 may be programmed such that when making this emergency call the mobile device 102 automatically includes information on the patient, the laboratory value which is outside the predefined ranges and the location of the patient.

Yet another possibility is that the medical app 122 upon determining that the laboratory value, which has been monitored, is outside the predefined range causes the mobile device 102 to emit a perceivable alarm, for example an alarm sound, vibration or a flashing light in order to inform the patient of his current condition.

Usually the execution of the medical app 122 will include the execution of a sequence of individual processes. For example, the execution of the sequence of processes may include a first process for determining the laboratory value of the patient, a second process for determining whether the laboratory value is within the predefined range, a third process for displaying the laboratory value to the patient, a fourth process for demanding a confirmation to initiate counter measures and a fifth process to actually initiate these counter measures. In this case the step of initiating counter measures should not be executed unless the step of demanding a confirmation from the patient has already been executed. To make sure that the individual processes of the medical app 122 are executed in a correct way, the central processing unit 108 of the mobile device 102 may further comprise a supervising entity or safety module 128. In this case the supervising entity or safety module 128 is embodied in a task, which is executed by the central processing unit 108 of the mobile device 102.

In accordance with embodiments of the invention the individual processes of the medical app 122, upon being executed by the central processing unit 108, create information which is forwarded to the supervising entity or safety module 128. Using this information the supervising entity or safety module 128 can then verify whether the medical app 122 is executed correctly and in case the supervising entity or safety module 128 determines that the medical app 122 is not working correctly, the supervising entity or safety module 128 is operable to interrupt the execution of the medical app 122.

As shown in FIG. 1 it is also possible to embody the supervising entity or safety module 106 in a separate module comprising a memory 116, a communication interface 118 and a central processing unit 120, wherein the central processing unit 120 is operable to execute a program module 130 for evaluating the information produced during execution of the medical app 122. Once the supervising entity or safety module 106 determines by evaluating the information received from the mobile device 102 that the execution of the medical app 122 is flawed, the supervising entity or safety module 106 is operable to interrupt the execution of the medical app 122. To this end it is necessary that the supervising entity or safety module 106 can directly influence the execution or the functionality of the central processing unit 108.

In accordance with embodiments of the invention the medical device 104 may be an infusion pump for the delivery of a fluid into a patient's body, such as an insulin pump for the delivery of insulin for diabetes treatment. The medical device 104 may be coupled to a sensor for sensing at least one physiological parameter of the patient, i.e. a laboratory value such as the blood glucose level of the patient.

The sensor and/or the medical device 104 may be implemented as a single or two separate implants such as for subcutaneous implantation into the patient's body. The signals delivered by the sensor are evaluated by the program module 124 which results in the determination of the physiological parameter which is then communicated to the mobile device 102 via the communication interface 112 of the medical device 104. The mobile device 102 may be implemented as a mobile telecommunication device, such as a smartphone.

The mobile device 102 executes the medical app 122 into which the value of the physiological parameter is entered. The medical app 122 implements a control algorithm that uses the physiological parameter as an input value for determining a value of the control parameter for controlling the rate of fluid delivery by the infusion pump. For example, in the case of a diabetes application for diabetes care, the control algorithm may implement any suitable prior art control algorithm for controlling the rate of insulin delivery into a patient's body depending on the measured blood glucose level and/or other additional parameters that may have been received or entered and stored on the mobile device 102.

The mobile device 102 sends the value of the control parameter to the medical device 104. The value of the control parameter is entered into the program module 126 for controlling the infusion pump in accordance with the value of the control parameter for adjusting the rate of fluid delivery correspondingly.

In order to improve the safety of the medical system considered here the correct functioning of the mobile device 102 is supervised by a testing module, that may be implemented as a supervising entity 128 that is implemented as a program module, or a safety module 106 that is implemented as a separate hardware unit.

Alternatively, there may both be a software implemented supervising entity 128 and a hardware implemented safety module 106 for maximum safety. In the following the hardware implemented safety module 106 is considered here by way of example.

Before the medical app 122 sends the value of the control parameter to the medical device 104, the medical app 122 sends 'information' to the safety module 106 that signals a testing request. In response to receipt of the testing request, execution of the program module 130 is invoked for execution of a testing routine.

Execution of the testing routine may encompass the interchange of several testing messages between the mobile device 102 and the safety module 106 for testing whether the mobile device 102 is in a functional state. In particular, the program module 130 may implement a validation service as described below in particular with respect to FIGS. 4 and 10.

In case execution of the program module 130 results in a positive testing result that indicates a functional state of the mobile device 102, a respective response is returned from the safety module 106 to the mobile device 102. The medical app 122 only sends the value of the control parameter to the medical device 104 for adjusting the rate of delivery of the infusion pump, if the safety module 106 returns a positive testing result.

If the testing result is negative, the safety module 106 may return an 'interrupt' for interrupting the execution of the medical app 122 and/or for causing the mobile device 102 for outputting a visual, acoustic and/or tactile alert signal for informing the patient as regards the malfunctioning of the mobile device and/or for putting the mobile device 102 into a safe state, such as by disabling the communication interface 111 such that the mobile device 102 is prevented from sending the value of the control parameter to the medical device 104.

Figure 2:
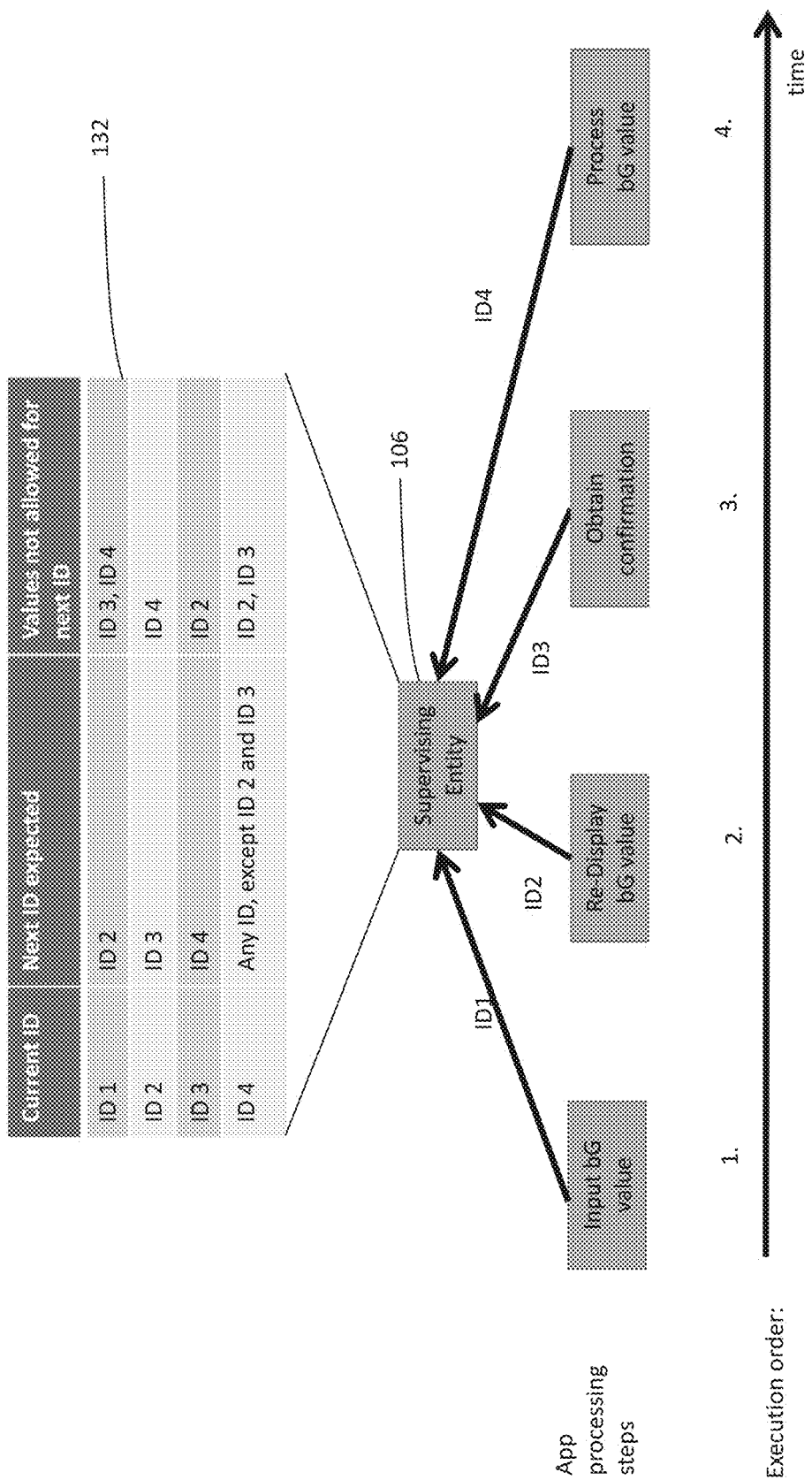
FIG. 2 is a schematic of a sequence of processes being supervised by the supervising entity or safety module using identifiers of the processes.

In the following, two possible approaches for supervising the execution of a sequence of processes will be discussed. A first possible embodiment of supervising a sequence of processes is depicted in FIG. 2. The process shown in FIG. 2 comprises four process steps. In this case the medical device 104 may be an insulin pump, which also has the functionality of monitoring the blood glucose level of a patient. In a first process step the blood glucose value is determined for example by demanding corresponding data from medical device 104 by the medical app 122. Once the blood glucose level has been input a second step of the process is to re-display the blood glucose value to the patient. In course of this re-displaying the medical app may demand a confirmation from the patient that appropriate counter measures may be executed. Only after obtaining this confirmation the blood glucose value may then further be processed in a fourth step for example such that in the end insulin shall be applied.

As described before, the execution of these four processes is supervised by the supervising entity or safety module 106. The supervising entity or safety module comprises a table 132, wherein the table is representative of the correct sequence of processing steps. To this end, table 132 may comprise the ID of a currently executed process, the ID of a next expected process and the values of IDs of processes which are not allowed to be executed subsequent to the current process.

In the situation depicted in FIG. 2 the process step of processing the blood glucose value, which is ID number 4, may not be executed until the confirmation of the patient has been obtained by executing the process with ID number 3. During execution the individual processes forward the ID of the currently executed process to the supervising entity or safety module 106. The supervising entity or safety module 106 then verifies whether the currently executed process is actually allowed to be processed. If the supervising entity or safety module 106 determines for example that the process with ID 3 is executed after the process with ID 1, the supervising entity or safety module interrupts the execution of the process.

In general it is possible to create the table 132 such that it contains information on the exact sequence of IDs or rules for IDs, which are not allowed to be executed after a certain ID of a prior process. The table 132 may also comprise the ID of a currently executed process and the process which has to be executed next. In general the approach depicted in FIG. 2 can be used to verify the correct sequence of processes during execution of the medical app.

Figure 3:
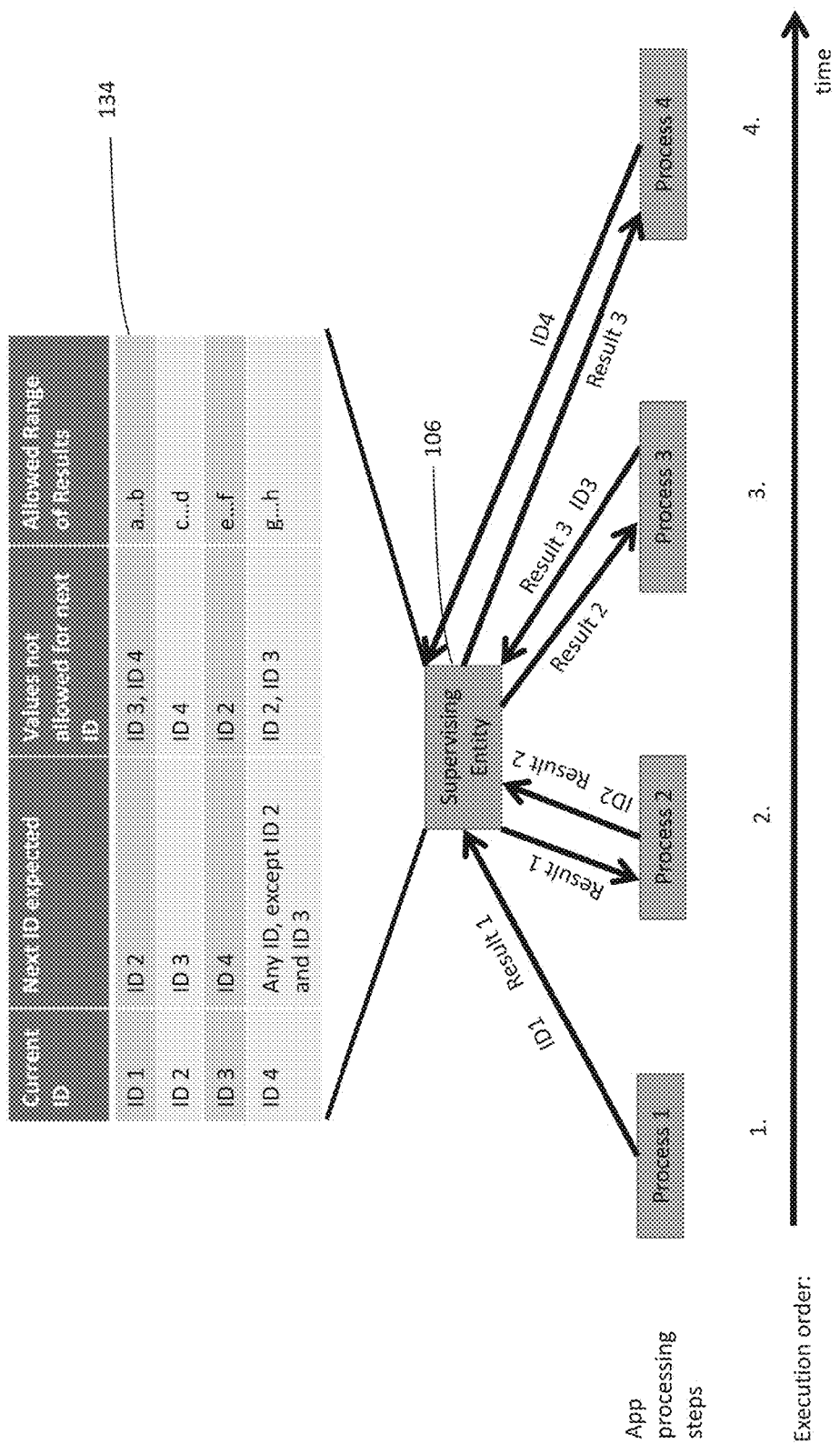
FIG. 3 is a schematic of a sequence of processes wherein the correct execution of the sequence is verified by a supervising entity or safety module by verifying the results of the individual processes.

In the approach depicted in FIG. 3 the supervising entity or safety module 106 as well comprises a table 134, but this time the supervising entity or safety module 106 is also operable to verify the intermediate results which are generated by the execution of the individual processes. For example, the process number 1, upon being executed by the central processing unit 108 of the mobile device 102, creates a result number 1. The supervising entity or safety module 106 may then access the table 134 and verify whether the result of process number 1 is within the allowed range of results that is in this case between values a and b. If this is the case, supervising entity or safety module 106 may then forward the result of process number 1 to process 2, such that process number 2 can be executed by the central processing unit. However, it is also possible that the process number 1 forwards the results of its execution to process number 2 by itself. Once process number 2 has been executed and created a result number 2, this result 2 is again forwarded to the supervising entity or safety module 106, wherein the supervising entity or safety module 106 verifies the result of process number 2 by looking up table 134. As described before, if the result number 2 is within the allowed range of results, supervising entity or safety module 106 forwards the result of process number 2 to process number 3 and so forth.

Note that in the situation depicted in FIG. 2, the sequence of processes will keep running until the supervising entity or safety module determines that a process is about to be executed, which is not allowed to be executed and then interrupts the execution of the sequence of processes. In the situation depicted in FIG. 3, the execution of a process depends on the confirmation of the correct execution of the prior process by the supervising entity or safety module 106. Thus, in the situation depicted in FIG. 2 the supervising entity or safety module only observes and intervenes if something goes wrong, wherein the supervising entity or safety module 106 depicted in FIG. 3 is directly involved in the sequence of processes of the medical app.

Note that it is also possible to design the supervising entity or safety module 106 depicted in FIG. 1, such that it also supervises the execution of the supervising entity or safety module 128 executed by the central processing unit 108 of the mobile device 102.

Figure 4:
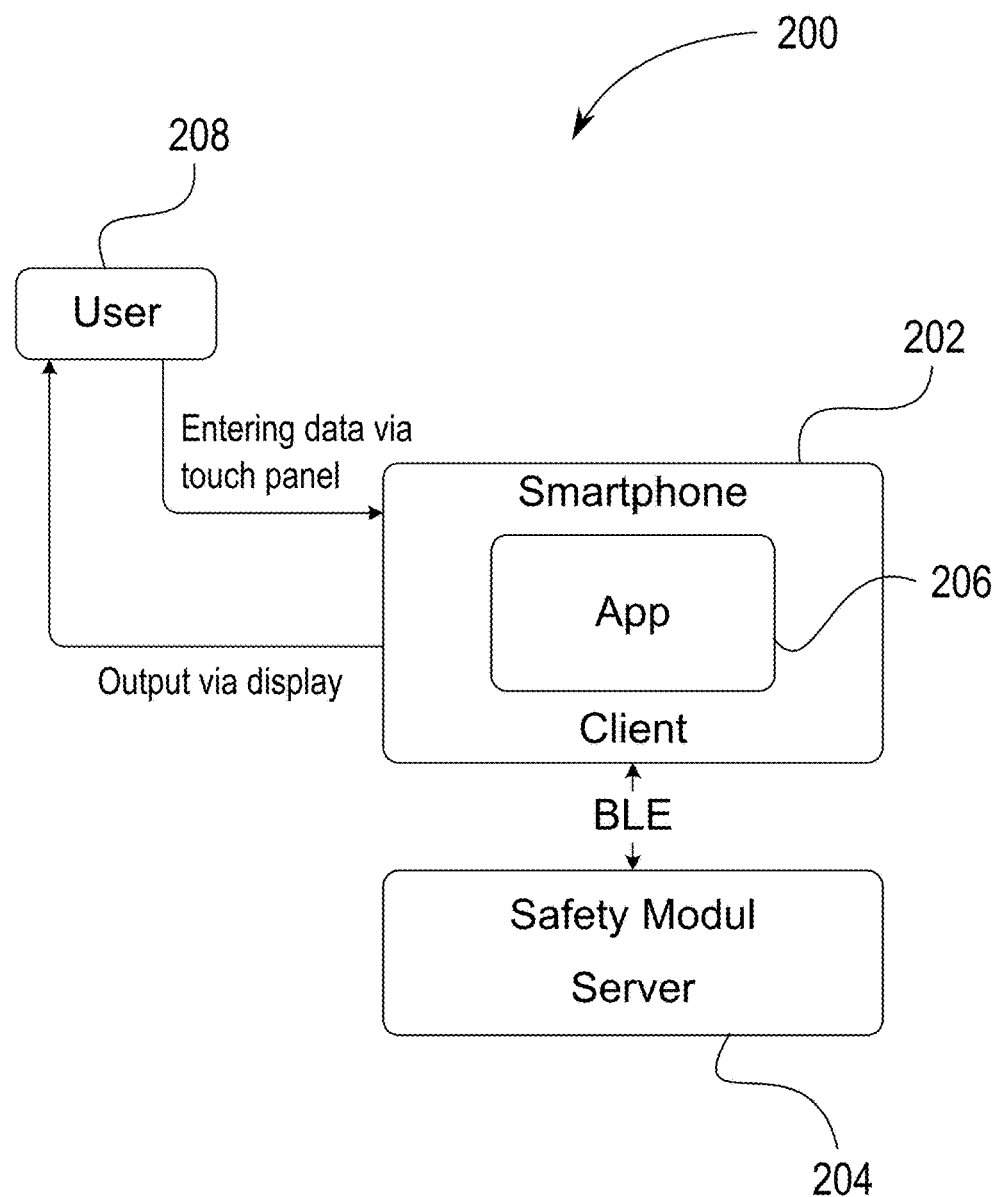
FIG. 4 is a block diagram of a system comprising a smartphone client and a supervising entity or safety module server.

FIG. 4 depicts a block diagram of a system 200 comprising a smartphone 202 as a mobile device and a supervising entity or safety module 204. The smartphone has a medical app 206 installed therein, which can be operated by a user 208 via a touch sensitive display of the smartphone 202. Via the touch sensitive display of the smartphone 202 the user 208 can call functions of the app 206 and receives a response about the status of the started functions. The app 206 is operable to communicate with the supervising entity or safety module 204 via a Bluetooth Low Energy (BLE) interface. The supervising entity or safety module 204 is a device which is physically separated from the smart phone 202 and thus gives a number of boundary conditions which have to be obeyed when constructing the supervising entity or safety module 204. The supervising entity or safety module 202 has its own power supply causing limited energy resources. For this reason a BLE interface is used.

The supervising entity or safety module 204 acts like a server, while the smart phone 202 can be understood as a client. As a client, the smart phone 202 is operable to connect to a plurality of BLE servers. This way the smart phone 202 does not occupy a physical interface. As a client, the smart phone 202 initiates the connection procedure sends request to the connected server. This way the smart phone 202 may inquire an identifier or can start the validation service of the supervising entity or safety module 204. The identifier serves as an entry into the BLE communication. The identifier is a single characteristic, which can be inquired and whose value is displayed to the user 208 in case of a successful data transfer.

Figure 5:
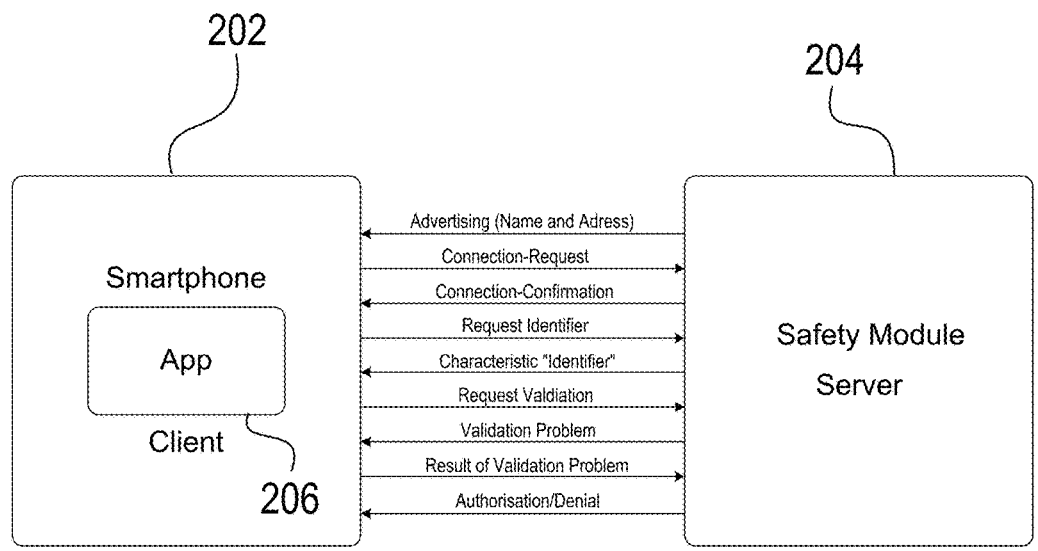
FIG. 5 is a schematic illustrating the data flow between the smartphone client and the supervising entity or safety module server.

The validation service is the main function of the supervising entity or safety module 204 and is meant to test the application 206 for correct execution. To this end the supervising entity or safety module 204 is operable to interfere with the activity of the application 206 in case the application 206 intends to execute a critical code sequence. The application 206 does not have the authorization to execute such a critical code sequence and has to request such an authorization from the supervising entity or safety module 204. To this end the supervising entity or safety module 204 may send a validation problem, which has to be solved by the smart phone 202. In case the result of the validation problem is correct, the application 206 will receive the authorization to execute the critical code sequence from the supervising entity or safety module 204. In case the result is not correct, the supervising entity or safety module 204 rejects the execution of the critical code sequence. The corresponding data flow between the smartphone client 202 and the supervising entity or safety module server 204 is illustrated in FIG. 5.

Figure 6:
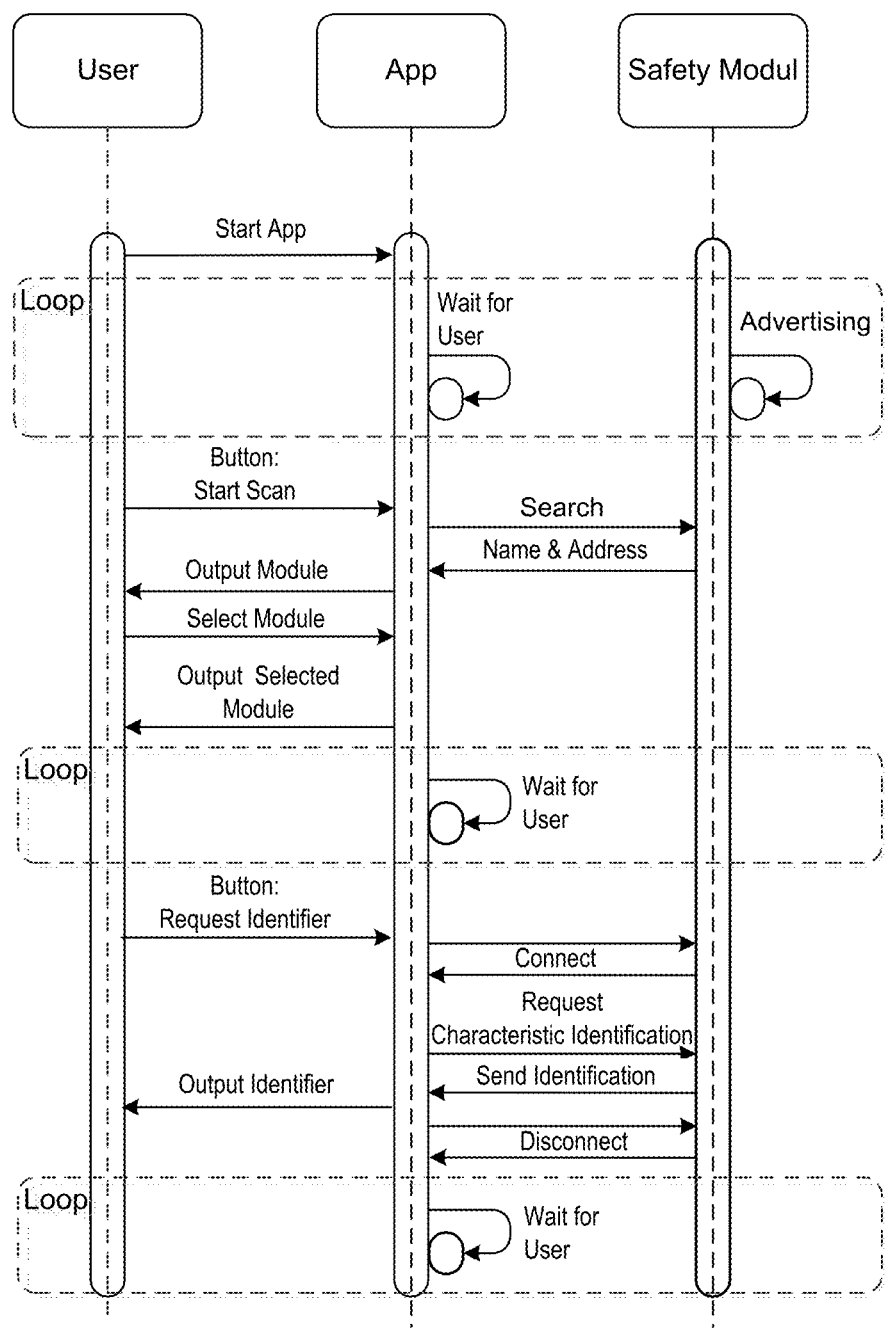
FIG. 6 is a sequence diagram illustrating the starting of the medical app and the pairing of a mobile device and the supervising entity or safety module.

FIG. 6 is a sequence diagram illustrating a method for starting the app 206, scanning for a supervising entity or safety module 204 and providing an identifier. The method starts with the user 208 starting the app 206 provided on the smart phone 202. The system 200 is then in a loop waiting for a user entry. Once the user 208 presses a button for starting a scanning procedure the application 206 starts a search for BLE devices. The fund BLE device then returns a name and address to the application 206 whereupon the application 206 displays this information to the user 208 via a display of the smart phone 202 the app 206 is running on. The user 208 then selects a detected module which is then returned to the user 208. Subsequently the application 206 is in a loop waiting for further user input. One the user 208 presses a button of the application 206 indicating that a request for an identifier shall be sent to the security module 204 the application 206 establishes a connection to the supervising entity or safety module 204 and receives a characteristic from the supervising entity or safety module 204. Further the application 206 request the identifier which is then returned by the supervising entity or safety module 204. The application 206 then displays the identifier and disconnects from the supervising entity or safety module 204. The application 206 returns to a loop waiting for further user input.

Figure 7:
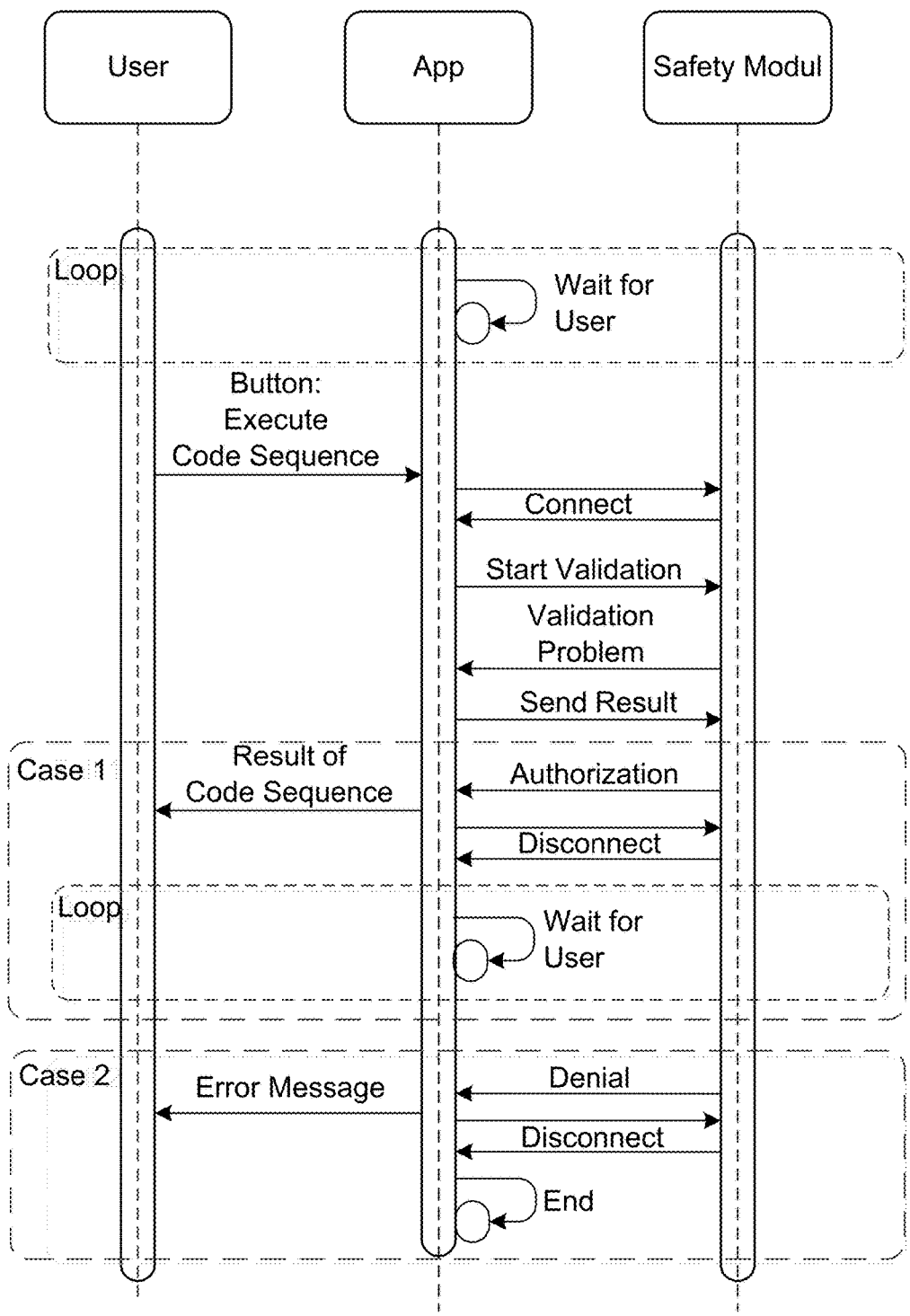
FIG. 7 is a sequence diagram illustrating the verification the correct operation of the mobile device by the supervising entity or safety module.

FIG. 7 is a sequence diagram of a method for verifying the correct operation of the mobile device 102 by the supervising entity or safety module 106 once a critical sequence of the medical app run 122 on the mobile device 102 is to be started. A critical sequence may for example be a sequence of method steps during which a critical medication has to be applied to the patient. To prevent the medical device 104 which is controlled by the medical app 122 run on the mobile device 102 from applying for example an incorrect dose rate due to a malfunctioning of the mobile device 102, the correct function of the medical app 122 should be validated prior to the execution of critical sequences.

In the initial state depicted in FIG. 7, the medical 122 is in a loop waiting for a user entry. If the user of the medical app 122 decides to start a critical sequence of a medical app 122, like for example the application of medicine, he may activate the corresponding function of the medical app 122 by pressing a corresponding button on the interface of the medical app 122. The medical app when addressed by the user may then check whether the sequence the user intends to use is a critical sequence. The medical app 122 may be configured not to run sequences which are marked as "critical" without permission of the supervising entity or safety module 106.

Thus if the medical app 122 determines, that the sequence activated by the user is critical, the medical app 122 or the mobile device 102 establishes a telecommunication connection with the supervising entity or safety module 106, for example via Bluetooth™ Low Energy. The medical app 122 then addresses the supervising entity or safety module to validate the medical app 122 thereby requesting the authorization to start the critical sequence activated by the user.

Upon being addressed by the medical app 122, the supervising entity or safety module 106 provides the medical app 122 with an arithmetic problem. This may for example be a simple addition of two numbers. The supervising entity or safety module 106 may then comprise a table comprising a plurality of number pairs and the corresponding result of their addition. Once the medical app 122 received the arithmetic problem, the medical app 122 solves the arithmetic problem using the CPU 108 of the mobile device 102 and returns the solution thus determined to the supervising entity or safety module 106. The supervising entity or safety module 106 then verifies, whether the arithmetic problem has been solved correctly.

If the supervising entity or safety module 106 determines, that the solution returned by the medical app 122 is correct, the supervising entity or safety module 106 authorizes the medical app 122 to execute the critical sequence activated by the user. The medical app 122 then executes the critical sequence and returns results of the critical sequence to the user if there are any results to be returned. Once the execution of the critical sequence has finished, the medical app 122 may then cause the mobile device 102 to disconnect from the supervising entity or safety module 106 and wait for further user entries.

If however the supervising entity or safety module 106 determines, that the solution returned by the medical app 122 is incorrect, the supervising entity or safety module 106 denies authorization of the medical app 122 to execute the critical sequence. The medical app 122 in response to receiving the denial may then display an error message to the user. Further the medical app 122 may cause the mobile device 102 to disconnect from the supervising entity or safety module 106 and to terminate the medical app 122, as the correct execution of sequences can no longer guaranteed.

It has to be noted that the user input of the diagrams depicted in FIGS. 6 and 7 is to be understood as an example for the exemplary application which is described. Other applications may have other inputs and outputs without departing from the scope of the claimed invention.

Figure 8:
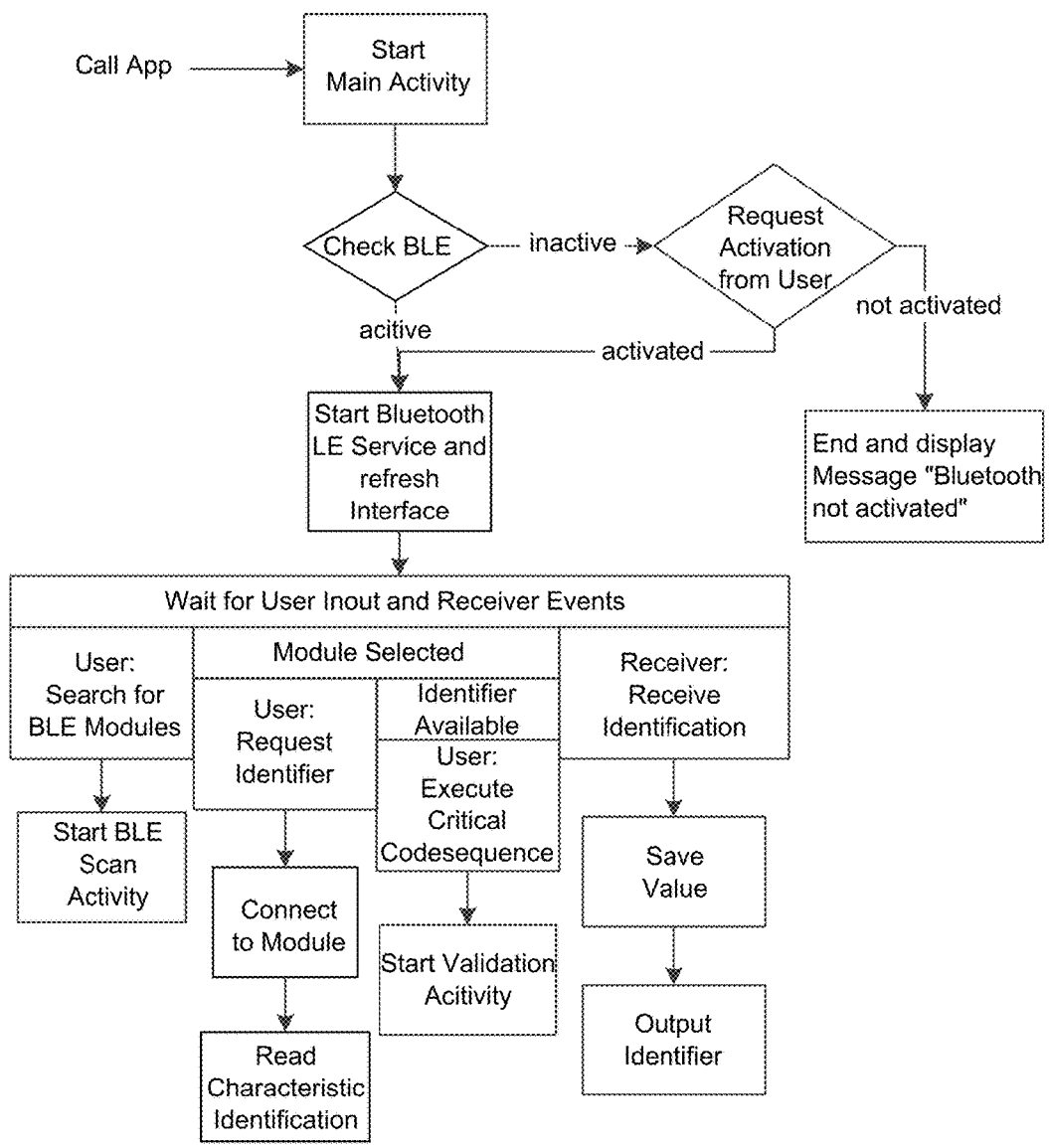
FIG. 8 is a flow diagram of the medical app.

FIG. 8 depicts a flow diagram of the main activity of the medical app 206. The main activity is the start activity and is meant to lead the user 208 for selecting functions of the application 206. Upon starting the application 206, the application 206 first checks, whether the BLE interface of the smart phone 202 is activated and in case the BLE interface is not activated asks user 208 whether the BLE interface shall be activated. Subsequently the user 208 may for example start the search for BLE modules by selecting the corresponding push-button. The search process for BLE modules will then be executed in another activity which is called when the user 208 presses the corresponding button. This BLE scan activity will later be described with reference to FIG. 9. Further the user 208 may start the inquiry for the identifier or the validation activity for a code sequence which is declared as being critical by pressing the corresponding button of the main activity. The validation activity will be described with reference to FIG. 10. It has to be noted that the flow chart of FIG. 8 only shows the part of the application 206 which is relevant for safeguarding the critical code sequences.

Figure 9:
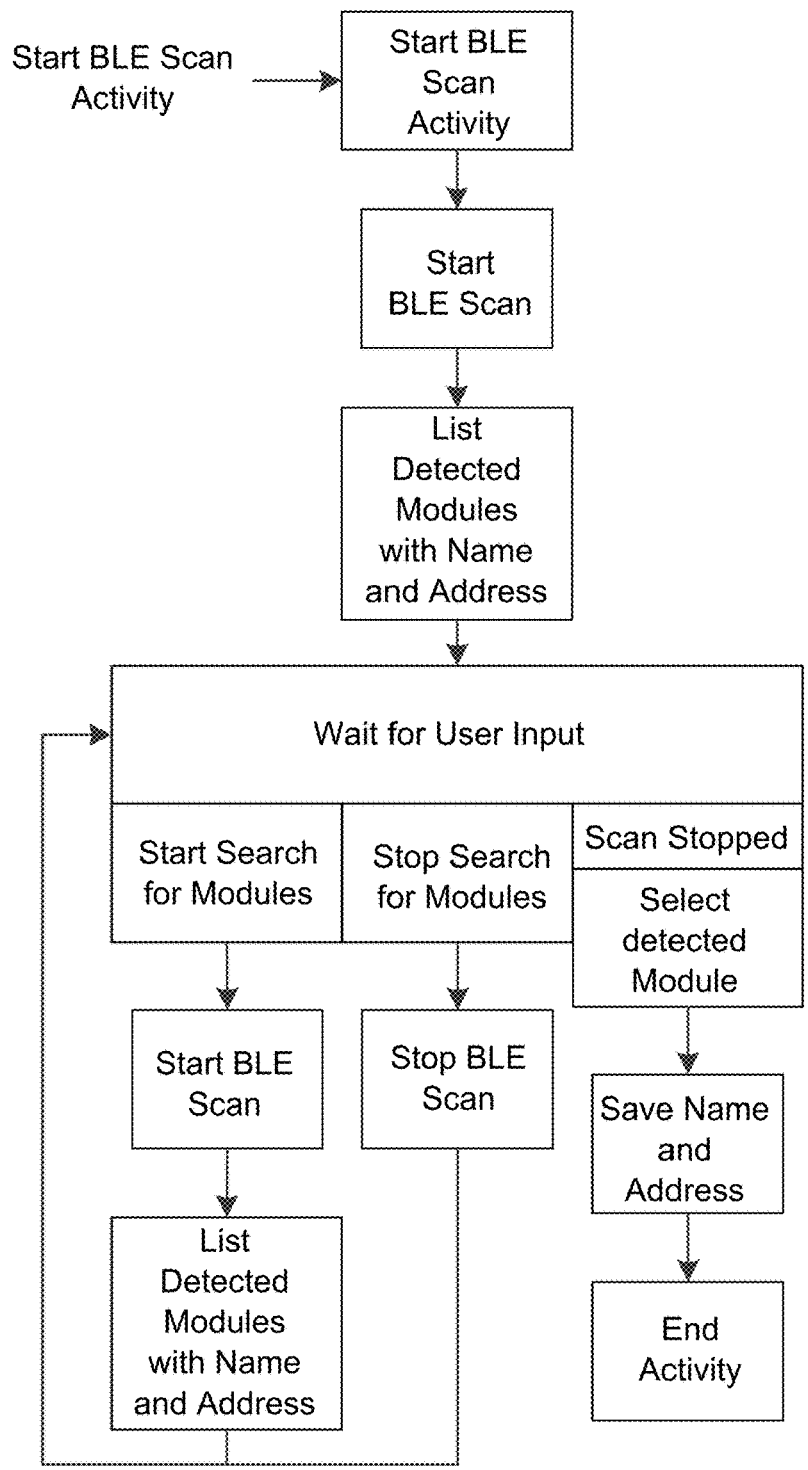
FIG. 9 is a flow chart of a scan process for BLE modules.

FIG. 9 depicts a flow diagram of the BLE scan activity. In the BLE scan activity a user 208 may conduct the searching procedure for BLE modules like a supervising entity or safety module 204. For example the BLE scan activity may be a list activity providing the plurality of functionalities for the displaying of data in the form of a list. Found BLE modules may be displayed with name and address and can be selected by the user 208 after the search for BLE modules has finished. The name and the address of the selected BLE module are then stored. In case the BLE scan activity is left during a search procedure, the search is stopped. A user 208 may himself stop the search procedure at any time using the corresponding button and may also restart the search procedure. For example the search procedure may have a time limit of 2 seconds.

Figure 10:
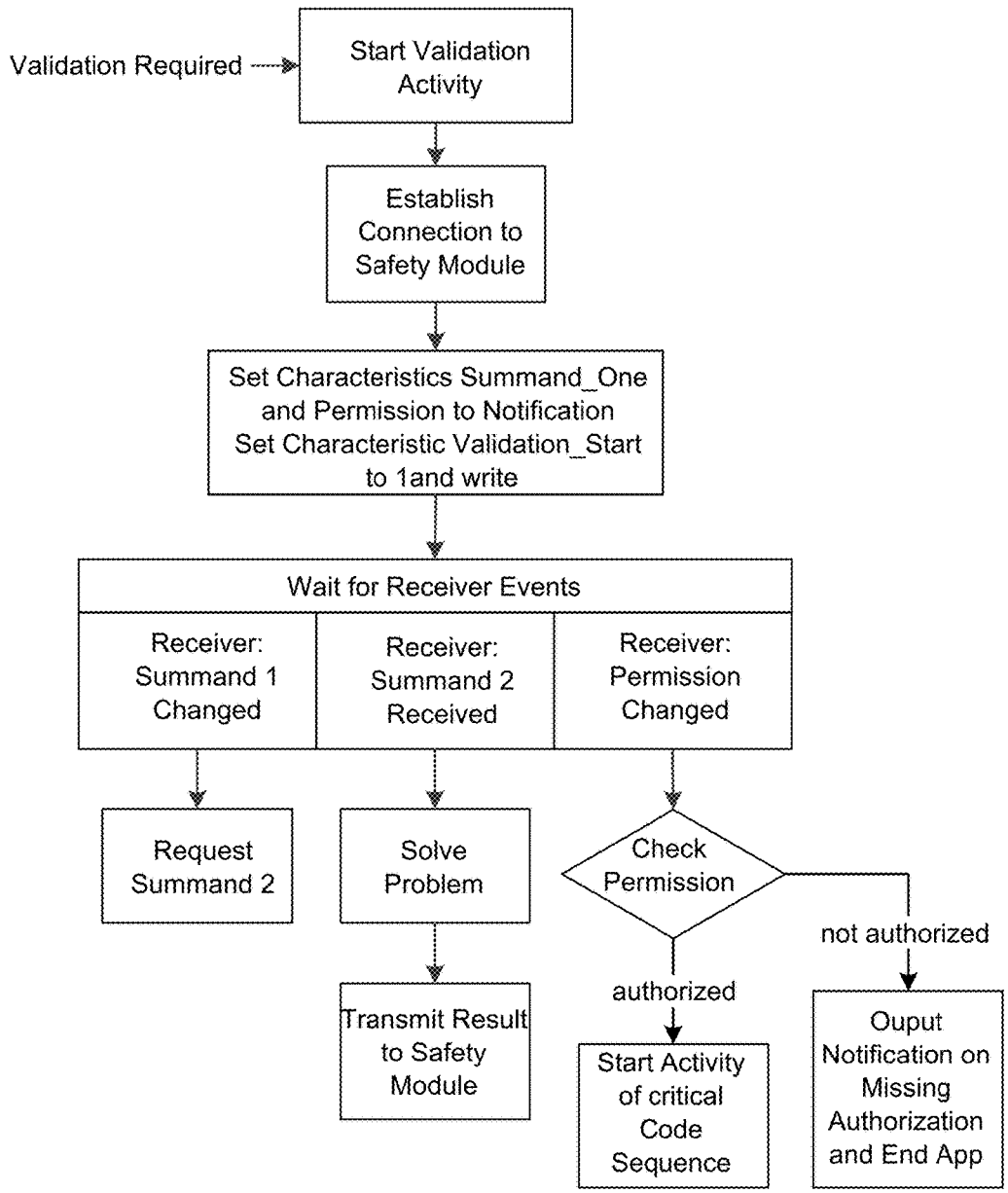
FIG. 10 is a flow chart of a validation process.

FIG. 10 depicts a flow diagram illustrating the validation activity for verifying the correct performance of the smart phone 202. The activity for validation is being called by the main activity in case the code sequence marked as being critical is meant to be executed. Once the validation activity has been called the validation activity takes further steps in order to contact the supervising entity or safety module 204 and start the validation service of the supervising entity or safety module 204. To this end a characteristic is descried on the supervising entity or safety module 204. The changing of this characteristic is interpreted by the supervising entity or safety module 204 as a starting signal for starting the validation service. The validation problem is then received in two steps. The supervising entity or safety module 204 equips the corresponding characteristics with values from a validation table comprised in the supervising entity or safety module 204. The value which is initialized second is set to "notification" upon starting the validation. As a result the application 206 will recognize the amended value of the characteristic.

In case the value has changed and this change has been submitted to the application 206, the second value is being read and the validation problem is solved by the smart phone 202. Upon sending the result of the validation problem the supervising entity or safety module 204 sends an integer value to the application, wherein the application is operable to interpret said integer value as an authorization or denial for executing the critical code sequence. In case of an authorization the activity of the code sequence marked as critical is started. In case of a denial the user is informed 208 that the request for executing has been denied and the application 206 is closed.

The validation problem described in FIG. 10 is a simple example of a validation problem only comprising a summation of two summands. It may however also be possible to use way validation problems which are more complex to solve.

Figure 11:
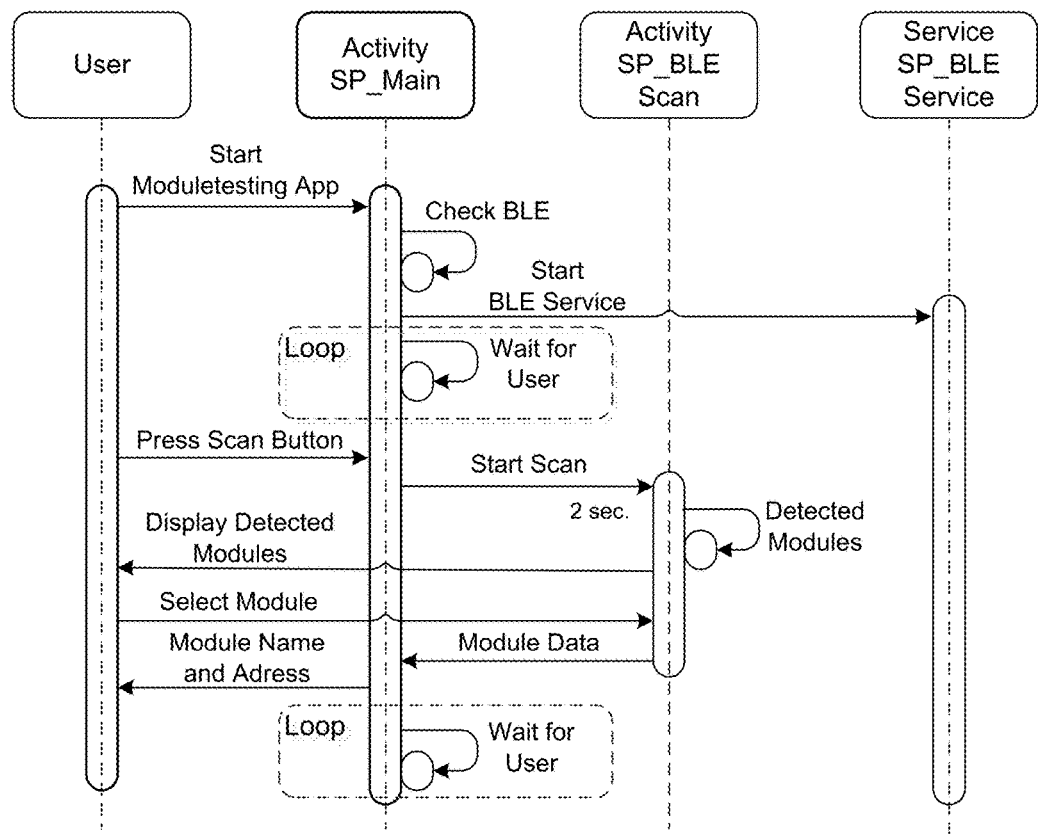
FIG. 11 is a sequence diagram for the startup of the medical app and the scanning for supervising entity or safety modules

FIG. 11 is a sequence diagram illustrating the start-up of the main activity of the application 206 as well as the scanning for BLE modules like the supervising entity or safety module 204. Upon starting the application 206 the status of the BLE interface of the smart phone 202 is checked and in case the interface is not yet activated the user 208 is asked whether the BLE interface shall be activated. In case the BLE interface of the smart phone 202 is activated, the user may initiate the search for BLE modules by activating the corresponding button for "start scan". Upon selection of one of the displayed BLE modules the corresponding data is passed on to the main activity for further processing and for displaying the data to the user 208.

Figure 12:
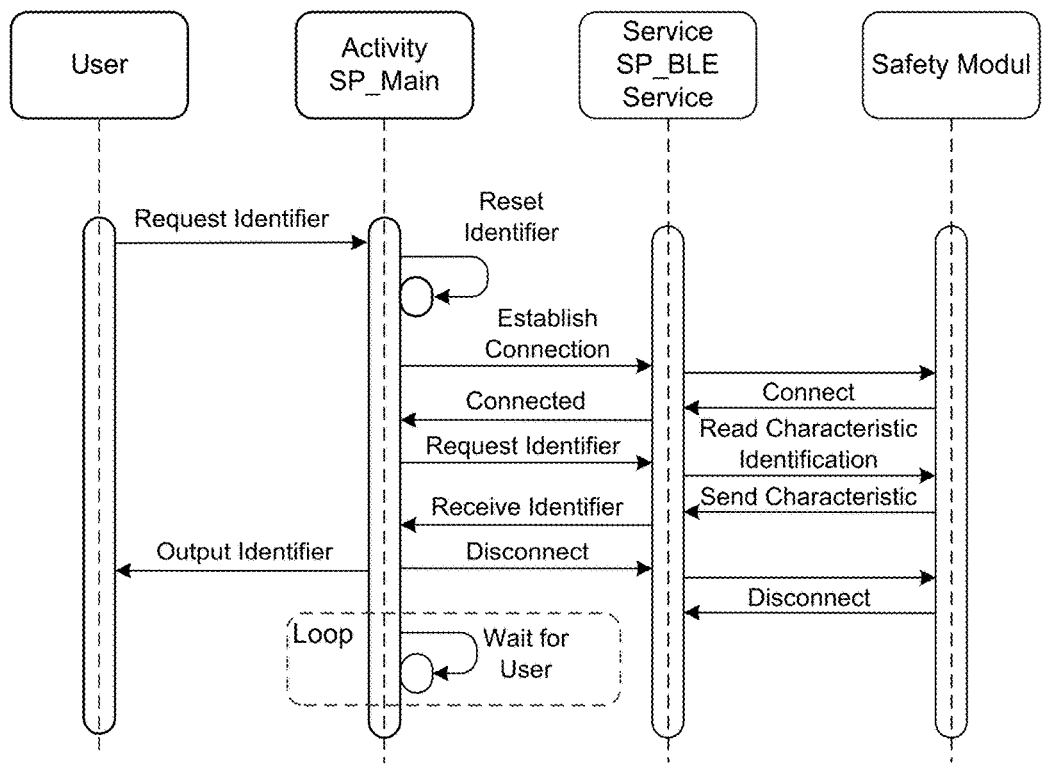
FIG. 12 is a sequence diagram illustrating the request of an identifier.

FIG. 12 depicts a sequence diagram illustrating the requesting of an identifier from the supervising entity or safety module 204. Upon activation of the button "request identifier" of the application 206 by the user 208 the selected BLE module is contacted using the BLE service and the characteristic "identification" is requested from the BLE module. This serves as an entry into the BLE communication. The value of the characteristic is displayed to the user 208 upon successful transmission of the characteristic. The identification is only provided by a supervising entity or safety module 204. In case the connected BLE module does not provide the identification, the connected BLE module is not a supervising entity or safety module 204. In this case the application 206 is closed with displaying a message indicating "supervising entity or safety module not found" has to be started all over again.

Figure 13:
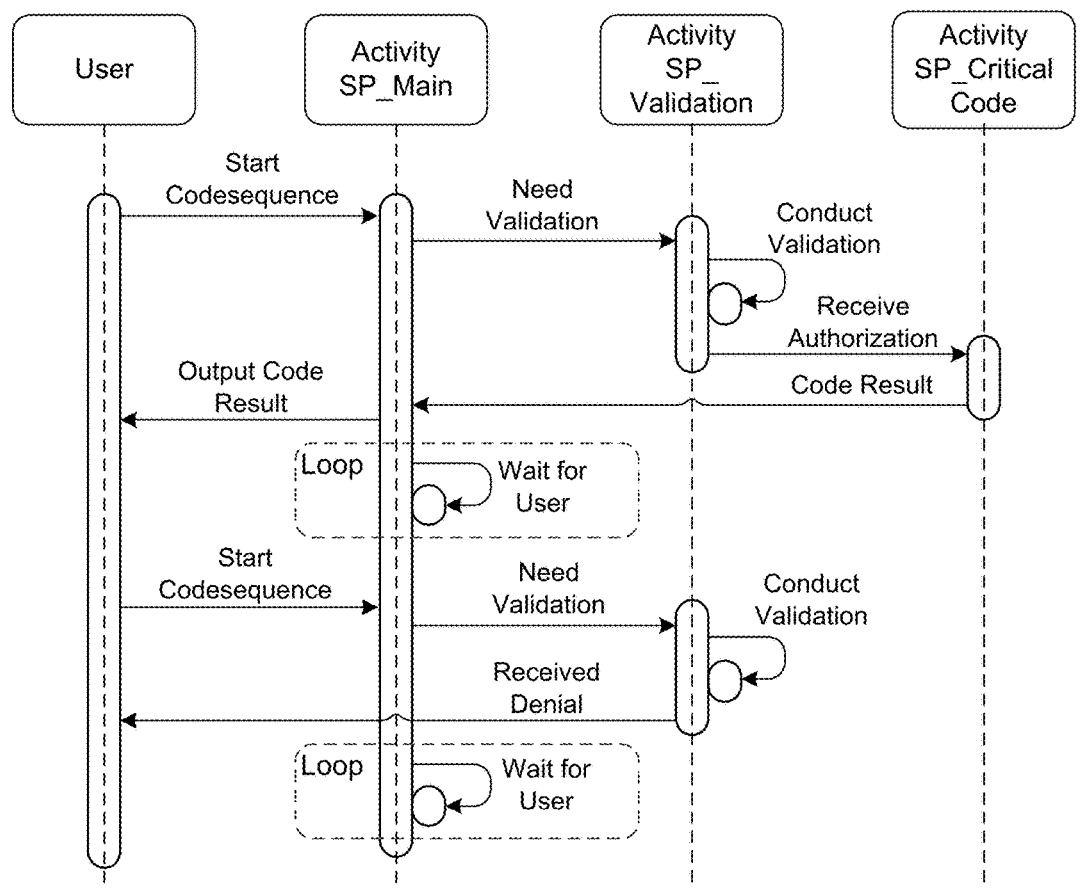
FIG. 13 is a sequence diagram illustrating the execution of a critical code sequence.
Figure 14:
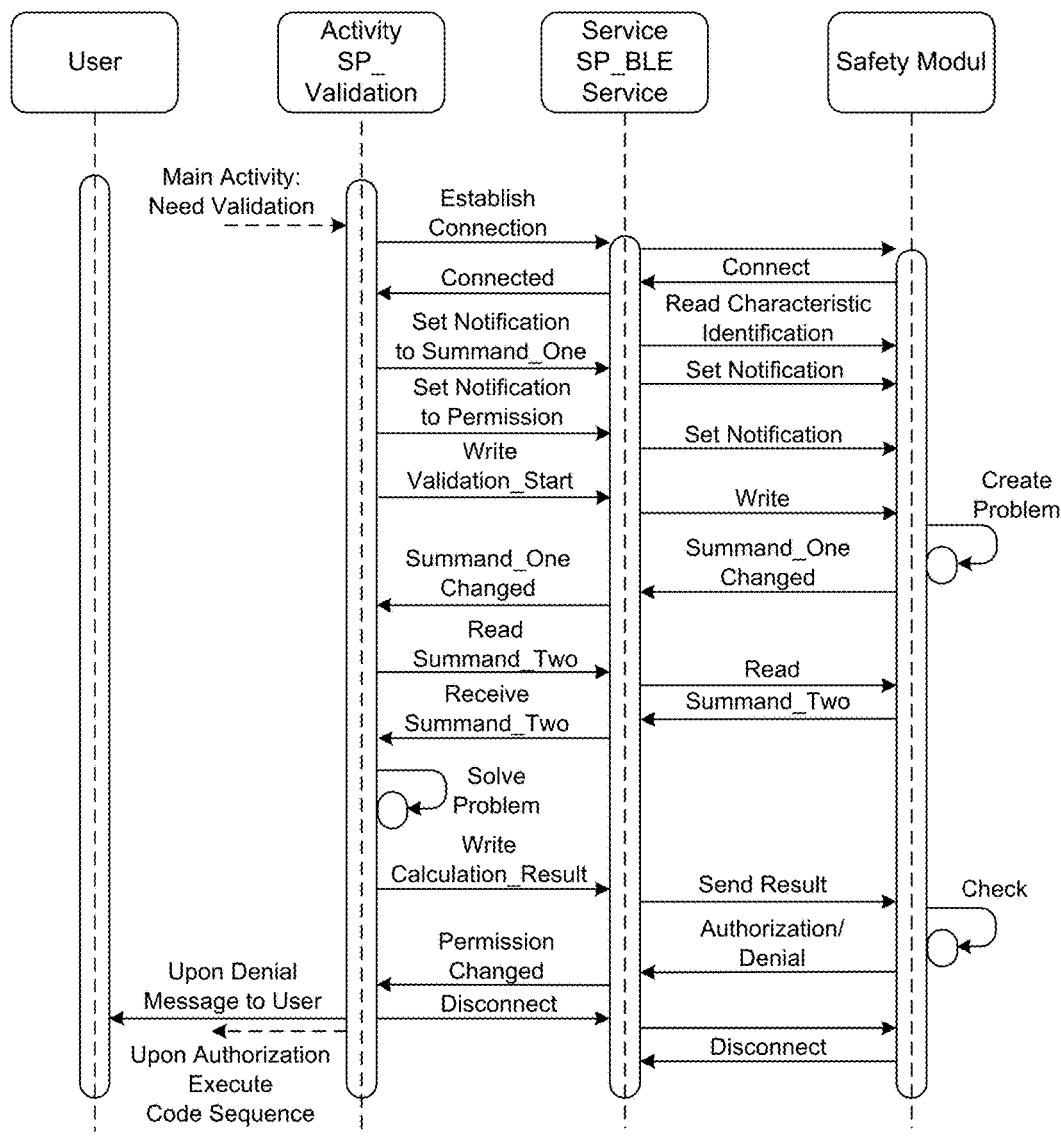
FIG. 14 is a sequence diagram illustrating the validation by the supervising entity or safety module.

FIG. 13 depicts a sequence diagram illustrating the execution of a critical code sequence. Upon activating the button for "start code sequence" the validation activity is started. The validation activity conducts a validation of the application 206 using the supervising entity or safety module 204. The validation is meant to verify whether the smart phone 202 and the application 206 work as expected. The validation procedure as such is illustrated in FIG. 14 and will be discussed in the following. In the first case depicted in FIG. 13 the validation leads to the supervising entity or safety module 204 returning an authorization to execute the critical code sequence. The result of the critical code sequence is then displayed to the user 208. In the second case the supervising entity or safety module 204 returns a denial which is provided to the user. In this case the critical code sequence is not executed.

FIG. 14 depicts a sequence diagram illustrating the validation process as performed by the supervising entity or safety module 204. As illustrated in FIG. 14 the validation procedure is triggered by the main activity of the application 206. To this end the validation activity upon being called by the main activity initializes the establishing of a connection with the supervising entity or safety module 204. Once the connection has been successfully established, the characteristics "summand one" and "permission" are set to "notification" in order to receive their corresponding value as soon as they are altered. Subsequently the validation process is being started by setting the characteristic "validation_start". To this end the supervising entity or safety module 204 creates the validation problem and initializes for example the two summands "summand_one" and "summand_two". First "summand_two" is written into the corresponding characteristic and subsequently "summand_one" is written. This writing procedure is recognized by the application 206 because of the notification functionality of BLE and as a result the application 206 retrieves the second summand via read-request. As a result the smart phone 202 retrieved the validation problem. This validation problem as to be solved by the smart phone 202 and the result has to be returned to the supervising entity or safety module 204 in a characteristic "calculation_result". The supervising entity or safety module 204 verifies the result using a look-up table and depending on the result of this verification sends an authorization or a denial in the characteristic "permission". The characteristic "permission" is set to "notification" as well and as a result is passed on to the validation activity for further processing. In case an authorization is received the code sequence is executed. In case a denial has been received the user is informed about the denial by a corresponding message and the activity is closed.

It has to be noted that the user input of the diagrams depicted in FIGS. 12, 13 and 14 is to be understood as an example for the exemplary application which is described. Other applications may have other inputs and outputs without departing from the scope of the claimed invention.

Further embodiments related to the invention are described in the attached scientific annex.

LIST OF REFERENCE NUMERALS

100 System
102 Mobile Device
104 Medical Device
106 safety module (Supervising Entity)
108 CPU
110 Communication Interface
112 Interface
114 CPU
116 Memory
118 Communication Interface
120 CPU
122 Medical App
124 Program Module
126 Program Module
128 Supervising entity
130 Program Module
132 Table
134 Table
200 System
202 Smartphone Client
204 Supervising entity or safety module Server
206 Application
208 User

The invention claimed is:

1. A method for generating a monitoring signal by monitoring laboratory values of a patient using a medical app, the medical app being executed on a mobile device of the patient, wherein the execution of the medical app on the mobile device of the patient is supervised by a supervising entity or safety module, the supervising entity or safety module comprising at least executable program instructions, the medical app comprising executable instructions for executing at least one sequence of processes for generating the monitoring signal, the processes comprising safety critical processes, the sequence of processes being triggered by the measurement of the laboratory values, such as the blood glucose level of the patient, the method comprising:

executing a first process of the sequence of processes, wherein the execution results in the generation of an information,
forwarding the information of the executed process to the supervising entity or safety module,
evaluating the received information by the supervising entity or safety module, and
executing a second process of the sequence of processes depending on the result of the evaluation;
wherein identifiers are assigned to the processes of the sequence, wherein the supervising entity or the safety module is operable to access a sequence table, wherein the sequence table comprises entries specifying allowed sequences of processes, wherein the information comprises the identifier of the second process, wherein the supervising entity or the safety module verifies whether the second process may be executed subsequent to the first process by looking up the sequence table, and wherein in response to determining that the second process is not allowed to be executed subsequent to the first process the supervising entity or safety module interrupts the execution of the sequence.

2. The method of claim 1, the sequence of processes comprising processes for
measuring or determining at least one laboratory value of the patient,
comparing the measured values to predefined ranges of permitted values, and
in response to determining that at least one of the measured or determined values
is beyond the predefined range, generating the monitoring signal.

3. The method of claim 1, wherein the monitoring signal is adapted to trigger the mobile device to make an emergency call.

4. The method of claim 1, wherein the mobile device is connected to a medical device of the patient, wherein the monitoring signal is adapted to trigger the medical device to apply medication such that the laboratory values of the patient are moved into the perimeters of the predefined range.

5. The method of claim 1, wherein the monitoring signal is adapted to trigger the mobile device to emit a perceivable alarm signal.

6. The method of claim 1, wherein the execution of the first process results in the generation of an intermediate result, wherein the intermediate result is passed on to the second process for further processing, wherein the information comprises the intermediate result, wherein the supervising entity or safety module verifies whether the intermediate result is within a defined range of results, wherein the second process of the sequence is only executed if the result has been determined to be within the defined range of results.

7. The method of claim 6, wherein in response to determining that the result is within the predefined range, the supervising entity or safety module generates a trigger signal and transmits the trigger signal to the mobile device, wherein the trigger signal when received by the mobile device-triggers the mobile device to execute the second process.

8. The method of claim 6, wherein in response to determining that the intermediate result is not within the defined range of results, the supervising entity or safety module brings the mobile device into a safe state.

9. The method of claim 8, wherein in the safe state the functionality of the mobile device is reversibly reduced, such that the mobile device is no longer operable to make an emergency call and/or trigger a medical device to apply medication and/or emit a perceivable alarm signal while in the safe state.

10. The method of claim 1, wherein the supervising entity or safety module is adapted to create a log file during execution of the sequence of processes, the log file comprising the identifiers of processes which have already been executed in course of the execution of the sequence of processes.

11. The method of claim 10, wherein the sequence table further comprises information specifying a set of processes which have to be executed prior to the execution of the second process, wherein supervising entity or safety module further verifies whether the set of processes has been executed by looking up the sequence table and comparing the identifiers of the set of processes with the identifiers comprised in the log file.

12. The method of claim 10, wherein the supervising entity or safety module deletes the log file if the sequence of processes has been completed successfully.

13. The method any of claim 1, wherein in response to determining that the second process is not allowed to be executed subsequent to the first process the supervising entity or safety module brings the mobile device into a safe state.

14. The method of claim 1 wherein the supervising entity or safety module is operable to address the mobile device to conduct a data processing algorithm, wherein the supervising entity or safety module further provides the mobile device with data for processing using the data processing algorithm, wherein the mobile device in response to being addressed by the supervising entity or safety module conducts the data processing algorithm thereby generating a result, wherein the supervising entity or safety module in response to the mobile device generating the result, verifies the result and in response to successfully verifying the result triggers the mobile device to execute the second process.

15. The method of claim 14, wherein the supervising entity or safety module addresses the mobile device to conduct the data processing algorithm if no allowed range for the intermediate result received with the information is defined.

16. The method of claim 1, wherein the mobile device is connected to a measurement entity, wherein the mobile device when executing the process of measuring at least one laboratory value of the patient addresses the measurement entity to conduct a corresponding measurement and return corresponding measurement values.

17. A system comprising a mobile device being connected to a supervising entity or safety module, wherein the mobile device is operable to execute at least one medical app, wherein the execution of the medical app on the mobile device is supervised by the supervising entity or safety module, the supervising entity or safety module comprising at least executable program instructions, the medical app comprising executable instructions for executing at least one sequence of processes for generating the monitoring signal, the processes comprising safety critical processes, the sequence of processes being triggered by the measurement of laboratory values of the patient, the mobile device being operable to execute a first process of the sequence of processes, wherein the execution results in the generation of an information and to forward the information to the supervising entity or safety module, wherein the supervising entity or safety module is adapted to evaluate the information, wherein the mobile device is further adapted to execute the second process of the sequence of processes depending on the result of the evaluation, wherein identifiers are assigned to the processes of the sequence, wherein the supervising entity or the safety module is operable to access a sequence table, wherein the sequence table comprises entries specifying allowed sequences of processes, wherein the information comprises the identifier of the second process, wherein the supervising entity or the safety module verifies whether the second process may be executed subsequent to the first process by looking up the sequence table, and wherein in response to determining that the second process is not allowed to be executed subsequent to the first process the supervising entity or safety module interrupts the execution of the sequence.

18. The system of claim 17, wherein the supervising entity or safety module comprises at least one processor, a telecommunication interface and a memory, wherein the memory comprises at least executable instructions for evaluating the information, wherein the processor of the supervising entity or safety module is adapted to execute the executable instructions comprised in the memory, and wherein the supervising entity or safety module is adapted to communicate with the mobile device using the communication interface.

* * * * *